(12) United States Patent
Lahm et al.

(10) Patent No.: US 7,211,270 B2
(45) Date of Patent: May 1, 2007

(54) ANTHRANILAMIDE INSECTICIDES

(75) Inventors: George Philip Lahm, Wilmington, DE (US); Thomas Paul Selby, Hockessin, DE (US); Thomas Martin Stevenson, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/527,863

(22) PCT Filed: Oct. 1, 2003

(86) PCT No.: PCT/US03/31677

§ 371 (c)(1),
(2), (4) Date: Mar. 16, 2005

(87) PCT Pub. No.: WO2004/033468

PCT Pub. Date: Apr. 22, 2004

(65) Prior Publication Data

US 2006/0052343 A1    Mar. 9, 2006

Related U.S. Application Data

(60) Provisional application No. 60/416,364, filed on Oct. 4, 2002.

(51) Int. Cl.
*A01N 25/00* (2006.01)
*C01F 7/10* (2006.01)
*C01F 7/02* (2006.01)
*C01D 231/00* (2006.01)

(52) U.S. Cl. .................. 424/405; 556/419; 546/14; 548/110; 548/406

(58) Field of Classification Search ........... 556/419; 424/405; 546/14; 548/110, 406
See application file for complete search history.

(56) References Cited

U.S. PATENT DOCUMENTS

| | | | |
|---|---|---|---|
| 6,835,847 B2 | 12/2004 | Bretschneider et al. | |
| 2004/0077597 A1 | 4/2004 | Bretschneider et al. | |

FOREIGN PATENT DOCUMENTS

| | | |
|---|---|---|
| WO | WO 01/070671 A2 | 9/2001 |
| WO | WO 02/062807 A1 | 8/2002 |

*Primary Examiner*—Alton Pryor

(57) ABSTRACT

This invention provides compounds of Formula I, N-oxides and suitable salts thereof

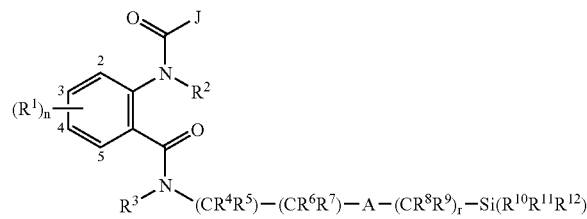

(I)

wherein A is O or $S(O)?m\#191$; J is a phenyl or heterocyclic ring as defined herein; and $R_1$ through $R_{12}$, n, m and r are as defined in the disclosure. Also disclosed are methods for controlling an invertebrate pest comprising contacting the invertebrate pest or its environment with a biologically effective amount of a compound of Formula I, an N-oxide thereof or a suitable salt of the compound (e.g., as a composition described herein). This invention also pertains to a composition for controlling an invertebrate pest comprising a biologically effective amount of a compound of Formula I, an N-oxide thereof or a suitable salt of the compound and at least one additional component selected from the group consisting of a surfactant, a solid diluent and a liquid diluent.

16 Claims, No Drawings

ANTHRANILAMIDE INSECTICIDES

This application is a 371 of PCT/US03/31677 filed Oct. 1, 2003, which claims benefit of 60/416,364 filed Oct. 4, 2002.

FIELD OF THE INVENTION

This invention relates to certain heterocyclic amides, their N-oxides, salts and compositions suitable for agronomic and nonagronomic uses, including those uses listed below, and a method of their use for controlling invertebrate pests in both agronomic and nonagronomic environments.

BACKGROUND OF THE INVENTION

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, and public and animal health is also important. Many products are commercially available for these purposes, but the need continues for new compounds that are more effective, less costly, less toxic, environmentally safer or have different modes of action.

PCT Publication WO01/070671 discloses N-acyl anthranilic acid derivatives of Formula i as arthropodicides

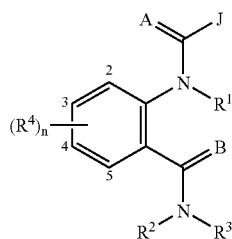

i wherein, inter alia, A and B are independently O or S; J is an optionally substituted phenyl ring, 5- or 6-membered heteroaromatic ring, naphthyl ring system or an aromatic 8-, 9- or 10-membered fused heterobicyclic ring system; $R^1$ and $R^3$ are independently H or optionally substituted $C_1$–$C_6$ alkyl; $R^2$ is H or $C_1$–$C_6$ alkyl; each $R^4$ is independently H, $C_1$–$C_6$ alkyl, $C_1$–$C_6$ haloalkyl, halogen or CN; and n is 1 to 4.

SUMMARY OF THE INVENTION

This invention provides a compound of Formula I, an N-oxide or agriculturally suitable salt thereof

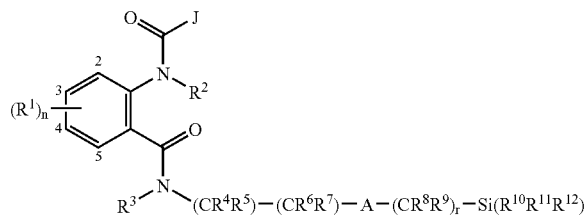

I wherein
A is O or $S(O)_m$;

J is a phenyl optionally substituted with one to four substituents independently selected from the group $R^{15}$; or J is a heterocyclic ring selected from the group consisting of

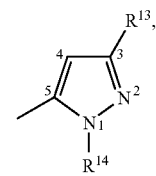

J-1

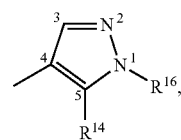

J-2

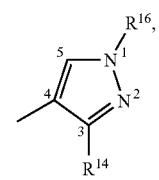

J-3

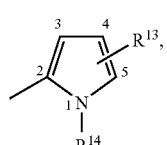

J-4

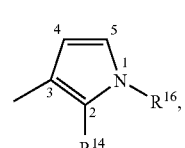

J-5

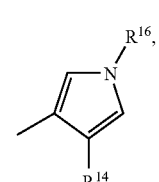

J-6

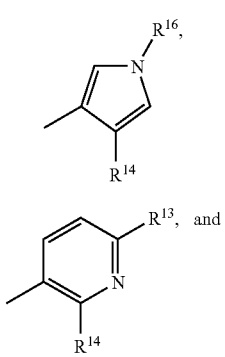

J-7

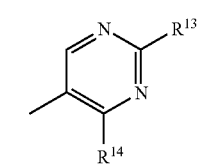

J-8 each $R^1$ is independently selected from the group consisting of $C_1$–$C_6$ alkyl, $C_2$–$C_6$ alkenyl, $C_2$–$C_6$ alkynyl, $C_3$–$C_6$ cycloalkyl, $C_1$–$C_6$ haloalkyl, $C_2$–$C_6$ haloalkenyl, $C_2$–$C_6$ haloalkynyl, $C_3$–$C_6$ halocycloalkyl, halogen, CN, $NO_2$, hydroxy, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl, $C_1$–$C_4$ haloalkylsulfonyl, $C_2$–$C_4$ alkoxycarbonyl, $C_2$–$C_4$ alkylaminocarbonyl, $C_3$–$C_5$ dialkylaminocarbonyl, $C_1$–$C_4$ alkylamino, $C_2$–$C_8$ dialkylamino, $C_3$–$C_6$ cycloalkylamino and $C_3$–$C_6$ trialkylsilyl; or each $R^1$ is independently selected from the group consisting of phenyl, benzyl and phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_4$–$C_7$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_8$ dialkylaminocarbonyl or $C_3$–$C_6$ trialkylsilyl;

$R^2$ is H; or $C_1$–$C_6$ alkyl, $C_2$–$C_6$ alkenyl, $C_2$–$C_6$ alkynyl or $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino; or $R^2$ is $C_2$–$C_6$ alkylcarbonyl, $C_2$–$C_6$ alkoxycarbonyl, $C_2$–$C_6$ alkylaminocarbonyl or $C_3$–$C_8$ dialkylaminocarbonyl;

$R^3$ is H, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy, $C_1$–$C_4$ alkylamino, $C_2$–$C_8$ dialkylamino, $C_3$–$C_6$ cycloalkylamino, $C_2$–$C_6$ alkoxycarbonyl or $C_2$–$C_6$ alkylcarbonyl;

$R^4$, $R^5$, $R^6$, $R^7$, $R^8$ and $R^9$ are each independently H, $C_1$–$C_4$ alkyl or $C_1$–$C_4$ haloalkyl;

$R^{10}$ and $R^{11}$ are each independently $C_1$–$C_4$ alkyl or $C_1$–$C_4$ alkoxy;

$R^{12}$ is $C_1$–$C_4$ alkyl, $C_1$–$C_4$ alkoxy or phenyl optionally substituted with one to three substituents selected from the group $R^{17}$;

each $R^{13}$ is independently selected from the group consisting of H, $C_1$–$C_6$ alkyl, $C_3$–$C_6$ cycloalkyl, $C_1$–$C_6$ haloalkyl, halogen, CN, $C_1$–$C_4$ alkoxy, $C_2$–$C_4$ alkoxycarbonyl, $C_1$–$C_4$ alkylthio, $C_1$–$C_4$ haloalkoxy, $C_1$–$C_4$ haloalkylthio, $C_1$–$C_4$ haloalkylsulfinyl and $C_1$–$C_4$ haloalkylsulfonyl;

$R^{14}$ is $C_1$–$C_6$ alkyl optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino; or phenyl optionally substituted with one to three substituents selected from $R^{17}$; or $R^{14}$ is

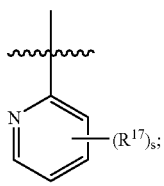

$R^{15}$ is $C_1$–$C_6$ alkyl, $C_3$–$C_6$ cycloalkyl, $C_1$–$C_6$ haloalkyl, halogen, CN, $C_1$–$C_4$ alkoxy, $C_1$–$C_4$ alkylthio, $C_1$–$C_4$ haloalkoxy, $C_1$–$C_4$ haloalkylthio, $C_1$–$C_4$ haloalkylsulfinyl or $C_1$–$C_4$ haloalkylsulfonyl; or $R^{15}$ is phenyl or pyridyl optionally substituted with one to three $R^{17}$;

$R^{16}$ is H, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl;

each $R^{17}$ is independently $C_1$–$C_6$ alkyl, $C_3$–$C_6$ cycloalkyl, $C_1$–$C_6$ haloalkyl, halogen, CN, $C_1$–$C_4$ alkoxy, $C_1$–$C_4$ alkylthio, $C_1$–$C_4$ haloalkoxy, $C_1$–$C_4$ haloalkylthio, $C_1$–$C_4$ haloalkylsulfinyl or $C_1$–$C_4$ haloalkylsulfonyl;

m is 0, 1 or 2;

n is 0, 1, 2, 3 or 4;

r is 0 or 1; and s is 0, 1 or 2.

This invention also provides a method for controlling invertebrate pests comprising contacting the invertebrate pest or its environment with a biologically effective amount of a compound of Formula I, an N-oxide thereof or a suitable salt of the compound (e.g., as a composition described herein). This invention also provides a method wherein the invertebrate pest or its environment is contacted with a biologically effective amount of a compound of Formula I or a composition comprising a compound of Formula I, an N-oxide thereof or a suitable salt of the compound and a biologically effective amount of at least one additional compound or agent for controlling invertebrate pests.

This invention also provides a composition for controlling invertebrate pests comprising a biologically effective amount of a compound of Formula I, an N-oxide thereof or a suitable salt of the compound and at least one additional component selected from the group consisting of a surfactant, a solid diluent and a liquid diluent. This invention also provides a composition comprising a biologically effective amount of a compound of Formula I, an N-oxide thereof or a suitable salt of the compound and an effective amount of at least one additional biologically active compound or agent.

DETAILS OF THE INVENTION

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio and butylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl isomers. "Alkylamino", "dialkylamino", and the like, are defined analogously to the above examples. "Cycloalkyl" includes, for example, cyclopropyl, cyclobutyl, cyclopentyl, and cyclohexyl. The term "cycloalkylamino" includes the same groups linked through a nitrogen atom such as cyclopentylamino and cyclohexylamino.

The term "hetero" in connection with rings or ring systems refers to a ring or ring system in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs. The terms "heteroaromatic ring or ring system" and "aromatic fused heterobicyclic ring system" includes fully aromatic heterocycles and heterocycles in which at least one ring of a polycyclic ring system is aromatic (where aromatic indicates that the Hutckel rule is satisfied). The heterocyclic ring or ring system can be attached through any available carbon or nitrogen by replacement of a hydrogen on said carbon or nitrogen.

The term "halogen", either alone or in compound words such as "haloalkyl", includes fluorine, chlorine, bromine or iodine. Further, when used in compound words such as "haloalkyl" or "halocycloalkyl", said alkyl or cycloalkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", "haloalkylthio", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH2C\equiv CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$.

Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$ and the different butylamino- or pentylaminocarbonyl isomers. Examples of "dialkylaminocarbonyl" include $(CH_3)_2NC(=O)$, $(CH_3CH_2)_2NC(=O)$, $CH_3CH_2(CH_3)NC(=O)$, $CH_3CH_2CH_2(CH_3)NC(=O)$ and $(CH_3)_2CHN(CH_3)C(=O)$.

The total number of carbon atoms in a substituent group is indicated by the "$C_i$–$C_j$" prefix where i and j are numbers from 1 to 8. For example, $C_1$–$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

In the above recitations, when a compound of Formula I is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g. $(R)_{i-j}$, then the number of substituents may be selected from the integers between i and j inclusive.

When a group contains a substituent which can be hydrogen, for example $R^{13}$, then, when this substituent is taken as hydrogen, it is recognized that this is equivalent to said group being unsubstituted. When the number of optional substituents on a group is 0, for example when n is 0, then it is recognized that this is equivalent to said group being unsubstituted. When a bond is depicted as floating, the substituent may be attached to any of the available carbons on the ring by replacement of hydrogen.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748–750, S. V. Ley, Ed., Pergamon Press; M. Tisler and B. Stanovnik in *Comprehensive Heterocyclic Chemistry*, vol. 3, pp 18–20, A. J. Boulton and A. McKillop, Eds., Pergamon Press; M. R. Grimmett and B. R. T. Keene in *Advances in Heterocyclic Chemistry*, vol. 43, pp 149–161, A. R. Katritzky, Ed., Academic Press; M. Tisler and B. Stanovnik in *Advances in Heterocyclic Chemistry*, vol. 9, pp 285–291, A. R. Katritzky and A. J. Boulton, Eds., Academic Press; and G. W. H. Cheeseman and E. S. G. Werstiuk in *Advances in Heterocyclic Chemistry*, vol. 22, pp 390–392, A. R. Katritzky and A. J. Boulton, Eds., Academic Press.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Preferred compounds for reasons of better activity and/or ease of synthesis are:

Preferred 1. Compounds of Formula I above, and N-oxides and suitable salts thereof, wherein
  A is $S(O)_m$;
  one of the $R^1$ groups is attached to the phenyl ring at the 2-position, and said $R^1$ is $C_1$–$C_4$ alkyl, $C_1$–$C_4$ haloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl or $C_1$–$C_4$ haloalkylsulfonyl;

$R^2$ and $R^3$ are each independently H, $C_1$–$C_4$ alkyl, $C_2$–$C_4$ alkenyl, $C_2$–$C_4$ alkynyl, $C_3$–$C_6$ cycloalkyl, $C_2$–$C_6$ alkylcarbonyl or $C_2$–$C_6$ alkoxycarbonyl;

$R^4$, $R^5$, $R^6$ and $R^7$ are each independently H or Me;

$R^8$ and $R^9$ are H;

$R^{10}$, $R^{11}$ and $R^{12}$ are Me;

n is 1 or 2; and r is 1.

Preferred 2. Compounds of Preferred 1 wherein
each $R^1$ is independently $CH_3$, $CF_3$, $OCF_3$, $OCHF_2$, $S(O)_pCF_3$, $S(O)_pCHF_2$, CN or halogen;
$R^2$ and $R^3$ are H; and
p is 0, 1 or 2.

Preferred 3. Compounds of Preferred 2 wherein
each $R^{13}$ is H, $CH_3$, $CF_3$, $CH_2CF_3$, $CHF_2$, $OCH_2CF_3$, $OCHF_2$ or halogen;
$R^{14}$ is phenyl optionally substituted with one to two substituents selected from $R^{17}$; or
$R^{14}$ is

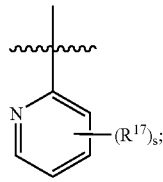

$R^{15}$ and $R^{17}$ are each independently $C_1$–$C_4$ alkyl, $C_1$–$C_4$ haloalkyl, halogen or CN;
each $R^{16}$ is $CH_2CF_3$ or $CHF_2$; and
s is 0 or 1.

Preferred 4. Compounds of Preferred 3 wherein
each $R^{13}$ is independently halogen, $OCH_2CF_3$, $OCHF_2$ or $CF_3$;
$R^{14}$ is

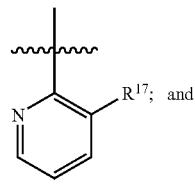

$R^{17}$ is F, Cl or Br.

Preferred 5. Compounds of Preferred 4 wherein
$R^6$ and $R^7$ are H.

Preferred 6. Compounds of Preferred 5 wherein
J is J-1, J-2, J-4 or J-8.

Preferred 7. Compounds of Preferred 6 wherein
J is J-1;
the $R^1$ group attached to the phenyl ring at the 2-position is $CH_3$, F, Cl or Br; a second $R^1$ group is attached to the phenyl ring at the 4-position position, and said second $R^1$ is CN, $CF_3$, F, Cl, Br or I;
$R^{13}$ is independently Cl, Br, $OCH_2CF_3$, or $CF_3$; and
n is 2.

The preferred compositions and preferred methods of use of the present invention are those which comprise the above preferred compounds.

The compounds of Formula I can be prepared by one or more of the following methods and variations as described in Schemes 1–15. The definitions of J, A, $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{16}$, $R^{17}$, n and r in the compounds of Formulae 1–49 below are as defined above in the Summary of the Invention unless indicated otherwise. $R^{1a}$ and $R^{1b}$ are defined as $R^1$. Compounds of Formula 5a, 5b and 13a are various subsets of the compounds of Formula 5 and 13

Compounds of Formula I can be prepared by the reaction of benzoxazinones of Formula 2 with amines of Formula 3 as outlined in Scheme 1.

Scheme 1

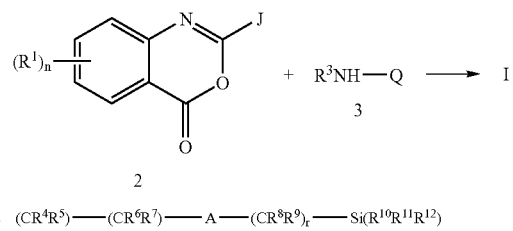

Q is $(CR^4R^5)$——$(CR^6R^7)$——A——$(CR^8R^9)_r$——$Si(R^{10}R^{11}R^{12})$

The reaction can be run neat or in a variety of suitable solvents including tetrahydrofuran, diethyl ether, dichloromethane and chloroform with optimum temperatures ranging from room temperature to the reflux temperature of the solvent. The general reaction of benzoxazinones with amines to produce anthranilamides is well documented in the chemical literature. For a review of benzoxazinone chemistry see Jakobsen et al., *Biorganic and Medicinal Chemistry* 2000, 8, 2095–2103 and references cited within. See also G. M. Coppola, *J. Heterocyclic Chemistry* 1999, 36, 563–588. For the synthesis of amines of Formula 3 see WO 02/062807.

Benzoxazinones of Formula 2 can be prepared by a variety of methods. Two methods that are especially useful are detailed in Schemes 2–3. In Scheme 2, a benzoxazinone of Formula 2 is prepared directly via coupling of a carboxylic acid of Formula 4 with an anthranilic acid of Formula 5.

Scheme 2

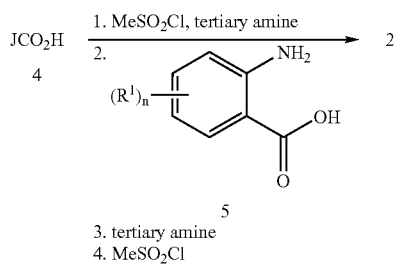

This involves sequential addition of methanesulfonyl chloride in the presence of a tertiary amine such as triethylamine or pyridine to a pyrazolecarboxylic acid of Formula 4, followed by the addition of an anthranilic acid of Formula 5, followed by a second addition of the tertiary amine and methanesulfonyl chloride. This method generally affords good yields of the benzoxazinone and is illustrated with greater detail in Example 1.

Scheme 3 depicts an alternate preparation for benzoxazinones of Formula 2 involving coupling of an acid chloride of Formula 7 with an isatoic anhydride of Formula 6 to provide the benzoxazinone of Formula 2 directly.

Scheme 3

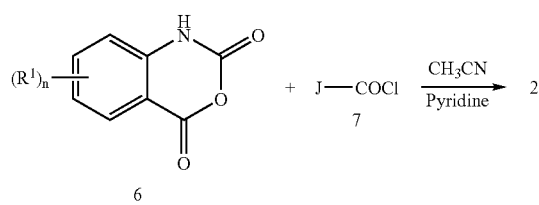

Solvents such as pyridine or pyridine/acetonitrile are suitable for this reaction. The acid chlorides of Formula 7 are available from the corresponding acids of Formula 4 by known methods such as chlorination with thionyl chloride or oxalyl chloride.

Anthranilic acids of Formula 5 are available by a variety of known methods. Many of these compounds are known. As shown in Scheme 4, anthranilic acids of Formula 5b containing an $R^{1b}$ substituent of chloro, bromo or iodo can be prepared by direct halogenation of an unsubstituted anthranilic acid of Formula 5a with N-chlorosuccinimide (NCS), N-bromosuccinimide (NBS) or N-iodosuccinimide (NIS) respectively in a suitable solvent such as N,N-dimethylformamide (DMF). The anthranilic acids of Formula 5b represent intermediates for a preferred set of compounds of Formula I.

Scheme 4

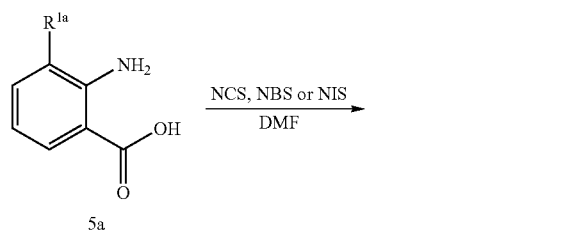

$R^{1b}$ is Cl, Br or I

Preparation of the isatoic anhydrides of Formula 6 can be achieved from isatins of Formula 9 as outlined in Scheme 5.

Scheme 5

Isatins of Formula 9 are available from aniline derivatives of Formula 8 following literature procedures such as F. D. Popp, *Adv. Heterocycl. Chem.* 1975, 18, 1–58 and J. F. M. DaSilva et al., *Journal of the Brazilian Chemical Society* 2001, 12(3), 273–324. Oxidation of isatin 9 with hydrogen peroxide generally affords good yields of the corresponding isatoic anhydride 6 (G. Reissenweber and D. Mangold, *Angew. Chem. Int. Ed. Engl.* 1980, 19, 222–223). Isatoic anhydrides are also available from the anthranilic acids 5 via many known procedures involving reaction of 5 with phosgene or a phosgene equivalent.

Heterocyclic acids 4, where J is equal to an optionally substituted pyrazole, pyrrole, pyridine or pyrimidine include those of Formula J-1 through J-8. More preferred analogs include those derived from the pyrazole acids that are substituted with $R^{14}$ as an optionally substituted phenyl or pyridyl. Procedures for the synthesis of representative examples of each are detailed in Schemes 6–15.

The synthesis of representative pyrazole carboxylic acids of Formula 13, which are related to Formula J-1 wherein $R^{14}$ is 2-pyridyl and attached to the nitrogen, is depicted in Scheme 6. Reaction of a pyrazole 10 with a 2-halopyridine of Formula 11 affords good yields of the 1-pyridylpyrazole 12 with good specificity for the desired regiochemistry. Metallation of a compound of Formula 12 with lithium diisopropylamide (IDA) followed by quenching of the lithium salt with carbon dioxide affords the pyrazole acids of Formula 13.

Scheme 6

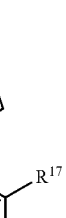

The starting pyrazoles of Formula 10 wherein $R^{13}$ is $CF_3$, Cl or Br are known compounds. Pyrazole 10 wherein $R^{13}$ is $CF_3$ can be prepared by literature procedures (*J. Fluorine Chem.* 1991, 53(1), 61–70). Pyrazoles 10 wherein $R^{13}$ is Cl or Br can also be prepared by literature procedures (H. Reimlinger and A. Van Overstraeten, *Chem. Ber.* 1966,99 (10), 3350–7). A useful alternative method for the preparation of 10 wherein $R^{13}$ is Cl or Br is depicted in Scheme 7. Metallation of the sulfamoyl pyrazole 14 with n-butyl-lithium followed by direct halogenation of the anion with either hexachloroethane (for $R^{13}$ being Cl) or 1,2-dibromotetrachloroethane (for $R^{13}$ being Br) affords the halogenated derivatives 15. Removal of the sulfamoyl group with trifluoroacetic acid (TFA) at room temperature proceeds cleanly and in good yield to afford the pyrazoles 10 wherein $R^{13}$ is Cl or Br respectively.

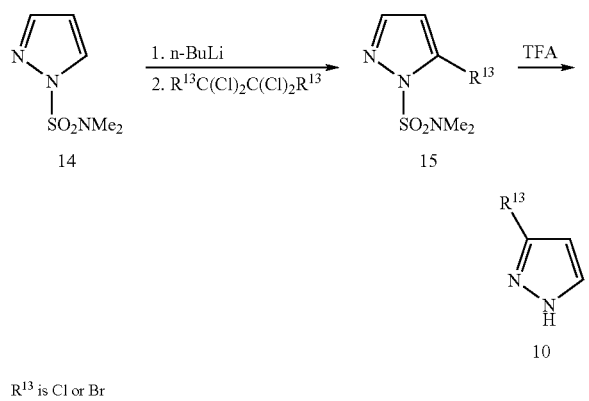

$R^{13}$ is Cl or Br

The synthesis of representative pyrazole acids of Formula 20, which are related to Formula J-2 wherein $R^{14}$ is 2-pyridyl and attached to the 5 position of the pyrazole ring, is depicted in Scheme 8. Reaction of the dimethylaminoylidene ketoester of Formula 18 with substituted hydrazines affords the pyridylpyrazoles 19. Preferred $R^{16}$ substituents include alkyl and haloalkyl, with trifluoroethyl especially preferred. The esters 19 are converted to the acids of Formula 20 by standard hydrolysis.

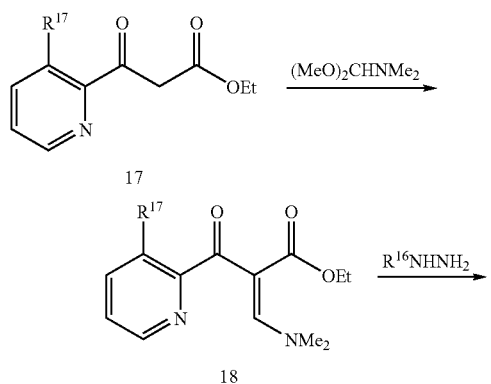

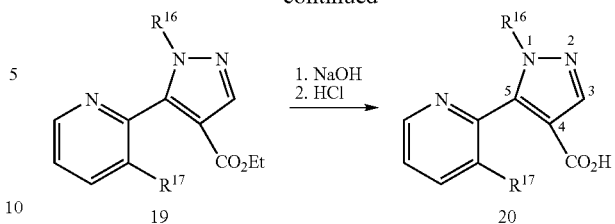

The synthesis of representative pyrazole acids of Formula 22, which are related to Formula J-3 wherein $R^{14}$ is 2-pyridyl and attached to the 3 position of the pyrazole ring as well as an alternative synthesis of Formula 20, is depicted in Scheme 9. Reaction of the dimethylaminoylidene ketoester of Formula 18, with hydrazine affords the pyrazole 21. Reaction of the pyrazole 21 with alkylating agents $R^{16}$-LG (wherein LG is a leaving group such as halogen (e.g., Br, I), $OS(O)_2CH_3$ (methanesulfonate), $OS(O)_2CF_3$, $OS(O)_2Ph-p-CH_3$ (p-toluenesulfonate), and the like) affords a mixture of pyridylpyrazoles. This mixture of pyrazole isomers is readily separated by chromatographic methods and converted to the corresponding acids 20 and 22. Preferred $R^{16}$ substituents include alkyl and haloalkyl groups.

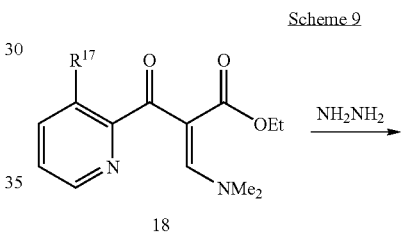

The synthesis of pyrrole acids of Formula 27, which are related to Formula J-4 wherein $R^{14}$ is 2-pyridyl and attached to the nitrogen of the pyrrole ring, is depicted in Scheme 10. 3-Chloro-2-aminopyridine 24 is a known compound (see *J. Heterocycl. Chem.* 1987, 24(5), 1313–16). A convenient preparation of 24 from 2-aminopyridine 23 involves protection, ortho-metallation, chlorination and subsequent deprotection. Treatment of a compound of Formula 24 with 2,5-dimethoxytetrahydrofuran affords pyrrole 25. Formylation of pyrrole 25 to the aldehyde of Formula 26 can be accomplished by using standard Vilsmeier-Haack formylation conditions. Halogenation of a compound of Formula 26 with N-halosuccinimides (NXS) occurs preferentially at the 4 position of the pyrrole ring. Oxidation of the halogenated aldehyde affords the pyridylpyrrole acids of Formula 27. The oxidation can be accomplished by using a variety of standard oxidation conditions.

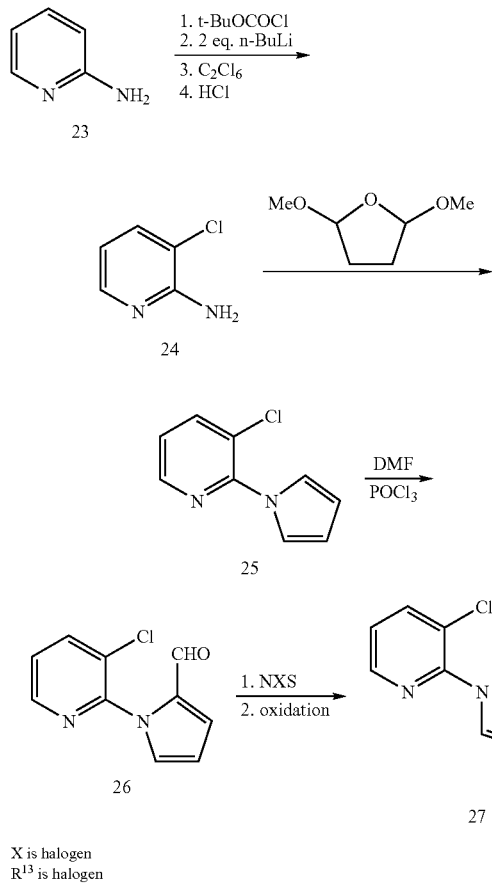

X is halogen
R[13] is halogen

The synthesis of pyrrole acids of Formula 33, which are related to Formula J-5 wherein R[14] is phenyl or 2-pyridyl and attached to the 2 position of the pyrrole ring, is depicted in Scheme 11. Cycloaddition of an allene of Formula 30 with an aryl sulfonamide of Formula 29 (see Pavri, N. P.; Trudell, M. L. *J. Org. Chem.* 1997, 62, 2649–2651) affords the pyroline of Formula 31. Treatment of a pyrroline of Formula 31 with tetrabutylammonium fluoride (TBAF) gives a pyrrole of Formula 32. Reaction of a pyrrole 32 with alkylating agents R[16]-LG (wherein LG is a leaving group as defined above) followed by hydrolysis affords a pyrrole acid of Formula 33.

Scheme 11

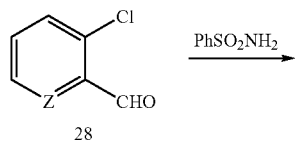

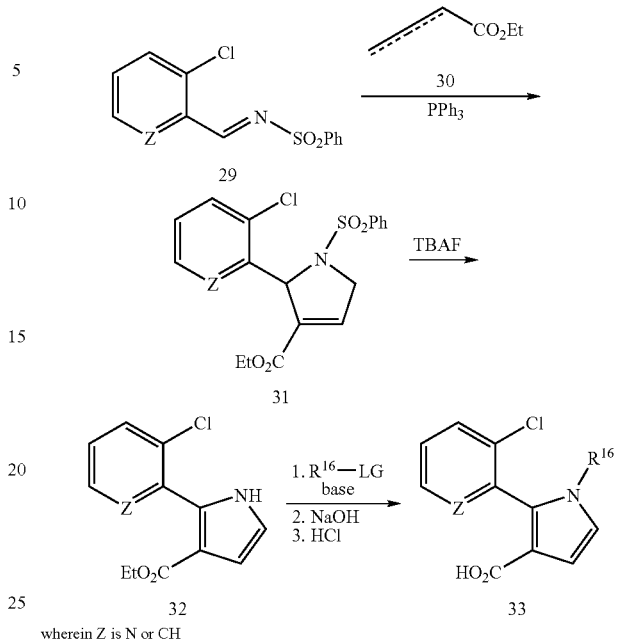

wherein Z is N or CH

The synthesis of pyrrole acids of Formula 36, which are related to Formula J-6 wherein R[14] is 2-chlorophenyl or 3-chloro-2-pyridyl, is depicted in Scheme 12. Reaction of a cinnamic ester of Formula 34 with tosylmethyl isocyanide (TosMIC) provides a pyrrole of Formula 35. For a leading reference to this method see, Xu, Z. et al. *J. Org. Chem.* 1998, 63, 5031–5041. Reaction of a compound of Formula 35 with an alkylating agent of Formula R[16]-LG (wherein LG is a leaving group as defined above) followed by hydrolysis of the ester affords a pyrrole acid of Formula 36.

Scheme 12

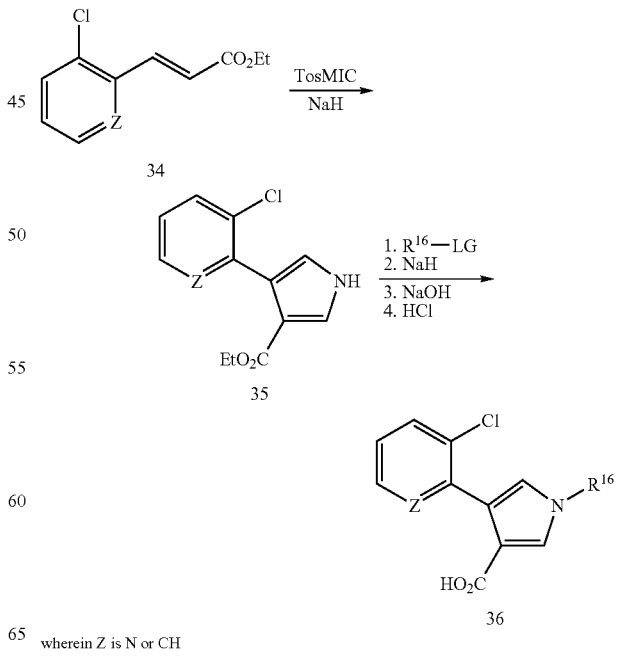

wherein Z is N or CH

The synthesis of pyridine acids of Formula 42, which are related to Formula J-7, is depicted in Scheme 13. This procedure involves the known synthesis of pyridines from β-ketoesters 40 and 4-aminobutenones 39. Substituent groups $R^{13}$ and $R^{14}$ include e.g. phenyl, alkyl and haloalkyl.

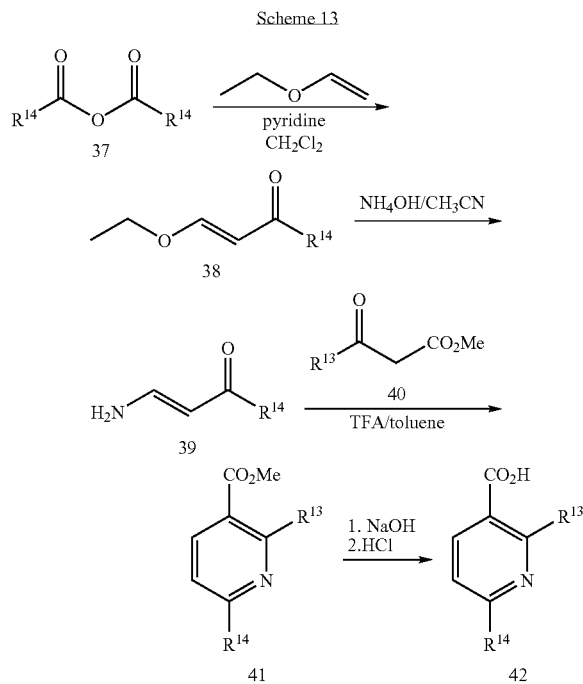

The synthesis of pyrimidine acids of Formula 46, which are related to Formula J-8, is depicted in Scheme 14. This procedure involves the known synthesis of pyrimidines from vinylidene ketoesters 44 and amidines. Substituent groups $R^{13}$ and $R^{14}$ include e.g. phenyl, alkyl and haloalkyl.

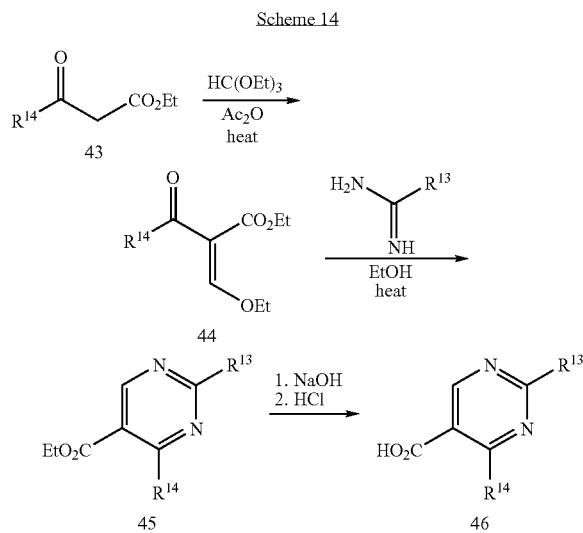

As an alternative to the method illustrated in Scheme 6, pyrazolecarboxylic acids of Formula 13a wherein $R^{13}$ is Cl or Br can be prepared by the method outlined in Scheme 15. Reaction of hydrazinopyridine 47 with diethyl maleate affords pyrazolone 48. Chlorination or bromination with phosphorus oxychloride or phosphorus oxybromide affords the halo derivatives of Formula 49. Oxidization of a compound of Formula 49 optionally in the presence of acid to give a pyrazole ester followed by conversion of the ester function to the carboxylic acid provides a compound of Formula 13a. The oxidizing agent can be hydrogen peroxide, organic peroxides, potassium persulfate, sodium persulfate, ammonium persulfate, potassium monopersulfate (e.g., Oxone®) or potassium permanganate.

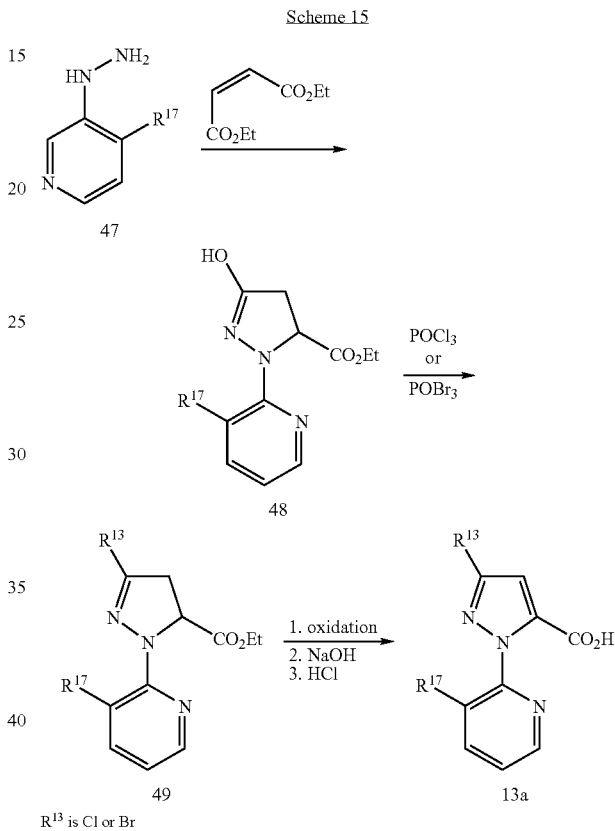

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent minxtures or where otherwise indicated. Parts and percentages for chromatographic solvent mixtures are by volume unless otherwise indicated. $^1$H NMR spectra are reported in ppm downfield from tetramethylsilane; s is singlet, d is doublet, t is triplet, q is quartet, m is multiplet, dd is doublet of doublets, dt is doublet of triplets, br s is broad singlet.

EXAMPLE 1

Preparation of 3-Bromo-N-[4-chloro-2-methyl-6-[[[1-methyl-2-[[(trimethylsilyl)methyl]thio]ethyl] amino]carbonyl]phenyl]-1-(3-chloro-2-pyridinyl)-1H-pyrazole-5-carboxamide Step A: Preparation of Ethyl 2-(3-Chloro-2-pyridinyl)-5-oxo-3-pyrazolidinecarboxylate A 2-L four-necked flask equipped with a mechanical stirrer, thermometer, addition funnel, reflux condenser, and nitrogen inlet was charged with absolute ethanol (250 mL) and an ethanolic solution of sodium ethoxide (21%, 190 mL, 0.504 mol). The mixture was heated to reflux at about 83° C. It was then treated with 3-chloro-2(1H)-pyridinone hydrazone (68.0 g, 0.474 mol). The mixture was re-heated to reflux over a period of 5 minutes. The yellow slurry was then treated dropwise with diethyl maleate (88.0 mL, 0.544 mol) over a period of 5 minutes. The reflux rate increased markedly during the addition. By the end of the addition all of the starting material had dissolved. The resulting orange-red solution was held at reflux for 10 minutes. After being cooled to 65° C., the reaction mixture was treated with glacial acetic acid (50.0 mL, 0.873 mol). A precipitate formed. The mixture was diluted with water (650 mL), causing the precipitate to dissolve. The orange solution was cooled in an ice bath. Product began to precipitate at 28° C. The slurry was held at about 2° C. for 2 hours. The product was isolated via filtration, washed with aqueous ethanol (40%, 3×50 mL), and then air-dried on the filter for about 1 hour. The title product compound was obtained as a highly crystalline, light orange powder (70.3 g, 55% yield). No significant impurities were observed by $^1$H NMR.

$^1$H NMR (DMSO-d$_6$) δ 1.22 (t, 3H), 2.35 (d, 1H), 2.91 (dd, 1H), 4.20 (q, 2H), 4.84 (d, 1H), 7.20 (dd, 1H), 7.92 (d, 1H), 8.27 (d, 1H), 10.18 (s, 1H).

Step B: Preparation of Ethyl 3-Bromo-1-(3-chloro-2-pyridinyl)-4,5-dihydro-1H-pyrazole-5-carboxylate A 1-L four-necked flask equipped with a mechanical stirrer, thermometer, reflux condenser, and nitrogen inlet was charged with acetonitrile (400 mL), ethyl 2-(3-chloro-2-pyridinyl)-5-oxo-3-pyrazolidinecarboxylate (i.e. the product of Step A) (50.0 g, 0.185 mol) and phosphorus oxybromide (34.0 g, 0.119 mol). The orange slurry was heated to reflux at 83° C. over a period of 20 minutes. The resulting turbid, orange solution was held at reflux for 75 minutes, at which time a dense, tan, crystalline precipitate had formed. The reflux condenser was replaced with a distillation head, and a cloudy, colorless distillate (300 mL) was collected. A second 1-L four-necked flask equipped with a mechanical stirrer was charged with sodium bicarbonate (45 g, 0.54 mol) and water (200 mL). The concentrated reaction mixture was added to the sodium bicarbonate slurry over a period of 5 minutes. The resulting two-phase mixture was stirred vigorously for 5 minutes, at which time gas evolution had ceased. The mixture was diluted with dichloromethane (200 mL) and then was stirred for 75 minutes. The mixture was treated with 5 g of Celite® 545 diatomaceous filter aid and then filtered to remove a brown, tarry substance. The filtrate was transferred to a separatory funnel. The brown organic layer (400 mL) was separated and then was treated with magnesium sulfate (15 g) and Darco® G60 activated charcoal (2.0 g). The resulting slurry was stirred magnetically for 15 minutes and then filtered to remove the magnesium sulfate and charcoal. The green filtrate was treated with silica gel (3 g) and stirred for several minutes. The deep blue-green silica gel was removed by filtration, and the filtrate was concentrated on a rotary evaporator. The product consisted of a light amber oil (58.6 g, 95% yield), which crystallized upon standing. The only appreciable impurity observed by $^1$H NMR was 0.3% acetonitrile.

$^1$H NMR (DMSO-d$_6$) δ 1.15 (t, 3H), 3.29 (dd, 1H), 3.60 (dd, 1H), 4.11 (q, 2H), 5.20 (dd, 1H), 6.99 (dd, 1H), 7.84 (d, 1H), 8.12 (d, 1H).

Step C: Preparation of Ethyl 3-Bromo-1-(3-chloro-2-pyridinyl)-1H-pyrazole-5-carboxylate A 1-L four-necked flask equipped with a mechanical stirrer, thermometer, reflux condenser, and nitrogen inlet was charged with ethyl 3-bromo-1-(3-chloro-2-pyridinyl)-4,5-dihydro-1H-pyrazole-5-carboxylate (i.e. the product of Step B) (40.2 g, 0.121 mol), acetonitrile (300 mL) and sulfuric acid (98%, 13.0 mL, 0.245 mol). The mixture self-heated from 22 to 36° C. upon adding the sulfuric acid. After being stirred for several minutes, the mixture was treated with potassium persulfate (48.0 g, 0.178 mol). The slurry was heated to reflux at 84° C. for 2 hours. The resulting orange slurry while still warm (50–65° C.) was filtered to remove a white precipitate. The filter cake was washed with acetonitrile (2×50 mL). The filtrate was concentrated to about 200 mL on a rotary evaporator. A second 1-L four-necked flask equipped with a mechanical stirrer was charged with water (400 mL). The concentrated reaction mass was added to the water over a period of about 5 minutes. The product was isolated via filtration, washed sequentially with aqueous acetonitrile (20%, 100 mL) and water (75 mL), and was then air-dried on the filter for 1 hour. The product consisted of a crystalline, orange powder (36.6 g, 90% yield). The only appreciable impurities observed by $^1$H NMR were about 1% of an unknown and 0.5% acetonitrile.

$^1$H NMR (DMSO-d$_6$) δ 1.09 (t, 3H), 4.16 (q, 2H), 7.35 (s, 1H), 7.72 (dd, 1H), 8.39 (d, 1H), 8.59 (d, 1H).

Step D: Preparation of 3-Bromo-1-(3-chloro-2-pyridinyl)-1H-pyrazole-5-carboxylic acid A 300-mL four-necked flask equipped with a mechanical stirrer, thermometer, and nitrogen inlet was charged with ethyl 3-bromo-1-(3-chloro-2-pyridinyl)-1H-pyrazole-5-carboxylate (i.e. the product of Step C) (98.5% pure, 25.0 g, 0.0756 mol), methanol (75 mL), water (50 mL), and sodium hydroxide pellets (3.30 g, 0.0825 mol). Upon adding the sodium hydroxide the mixture self-heated from 29 to 34° C. and the starting material began to dissolve. After being stirred for 90 minutes under ambient conditions, all of the starting material had dissolved. The resulting dark orange solution was concentrated to about 90 mL on a rotary evaporator. The concentrated reaction mixture was then diluted with water (160 mL). The aqueous solution was extracted with ether (100 mL). Then the aqueous layer was transferred to a 500-mL Erlenmeyer flask equipped with a magnetic stirrer. The solution was treated dropwise with concentrated hydrochloric acid (8.50 g, 0.0839 mol) over a period of about 10 minutes. The product was isolated via filtration, reslurried with water (2×40 mL), cover washed once with water (25 mL), and then air-dried on the filter for 2 hours. The product consisted of a crystalline, tan powder (20.9 g, 91% yield). The only appreciable impurities observed by $^1$H NMR were about 0.8% of an unknown and 0.7% ether.

$^1$H NMR (DMSO-$d_6$) δ 7.25 (s, 1H), 13.95 (br s, 1H), 8.56 (d, 1H), 8.25 (d, 1H), 7.68 (dd, 1H).

Step E: Preparation of 2-[3-Bromo-1-(3-chloro-2-pyridinyl)-1H-prazol-5-yl]-6-chloro-8-methyl-4H-3,1 -benzoxazin-4-one Methanesulfonyl chloride (1.0 mL, 1.5 g, 13 mmol) was dissolved in acetonitrile (10 mL), and the mixture was cooled to −5° C. A solution of 3-bromo-1-(3-chloro-2-pyridinyl)-1H-pyrazole-5-carboxylic acid (i.e. the product of Step D) (3.02 g, 10 mmol) and pyridine (1.4 mL, 1.4 g, 17 mmol) in acetonitrile (10 mL) was added dropwise over 5 minutes at −5 to 0° C. A slurry formed during the addition. The mixture was stirred 5 minutes at this temperature, and then a mixture of 2-amino-3-methyl-5-chlorobenzoic acid (1.86 g, 10 mmol) and pyridine (2.8 mL, 2.7 g, 35 mmol) in acetonitrile (10 mL) was added, rinsing with more acetonitrile (5 mL). The mixture was stirred 15 minutes at −5 to 0° C., and then methanesulfonyl chloride (1.0 mL, 1.5 mL, 13 mmol) in acetonitrile (5 mL) was added dropwise over 5 minutes at a temperature of −5 to 0° C. The reaction mixture was stirred 15 minutes more at this temperature, then allowed to warm slowly to room temperature, and stirred 4 h. Water (20 mL) was added dropwise, and the mixture was stirred 15 minutes. Then the mixture was filtered, and the solids were washed with 2:1 acetonitrile-water (3×3 mL), then with acetonitrile (2×3 mL), and dried under nitrogen to afford the title product as a light yellow powder, 4.07 g (90.2% crude yield), melting at 203–205° C. HPLC of the product using a Zorbax® RX-C8 chromatography column (4.6 mm×25 cm, eluent 25–95% acetonitrile/ pH 3 water) showed a major peak corresponding to the title compound and having 95.7% of total chromatogram peak area.

$^1$H NMR (DMSO-$d_6$) δ 1.72 (s, 3H) 7.52 (s, 1H), 7.72–7.78 (m, 2H), 7.88 (m, 1H), 8.37 (dd, 1), 8.62 (dd, 1H).

Step F: Preparation of 3-Bromo-N-[4-chloro-2-methyl-6-[[[1-methyl-2-[[(trimethylsilyl)methyl]thio]ethyl]amino] carbonyl]phenyl]-1-(3-chloro-2-pyridinyl)-1H-pyrazole-5-carboxamide To a solution of 2-[3-bromo-1-(3-chloro-2-pyridinyl)-1H-pyrazol-5-yl]-6-chloro-8-methyl-4H-3,1-benzoxazin-4-one (i.e. the benzoxazinone product of Step E) (0.23 g, 0.51 mmol) in tetrahydrofuran was added 1-trimethylsilylmethylthio-2-propylamine (0.103 g, 0.58 mmol), and the reaction mixture was heated to 80° C. for 3 hours and then cooled to room temperature. The tetrahydrofuran solvent was evaporated under reduced pressure, and the residual solid was chromatographed on silica gel with hexanes/ethyl acetate as eluent (5:1) to afford the title compound, a compound of the present invention, as a white solid (73 mg), m.p. 151–153° C.

$^1$H NMR (CDCl$_3$) δ 0.097 (s, 9H), 1.30 (d, 3H), 1.83 (s, 2H), 2.19 (s, 3H), 2.70 (d, 2H), 4.32 (m, 1H), 6.22 (bd, 1H), 7.22 (m, 2H), 7.05 (s, 1H), 7.28 (m, 2H), 7.38 (dd, 1H), 7.84 (dd, 1H), 8.45 (dd, 1H), 10.10 (bs, 1H).

By the procedures described herein together with methods known in the art, the following compounds of Tables 1 to 8 can be prepared. The following abbreviations are used in the Tables: Me is methyl and CN is cyano.

TABLE 1

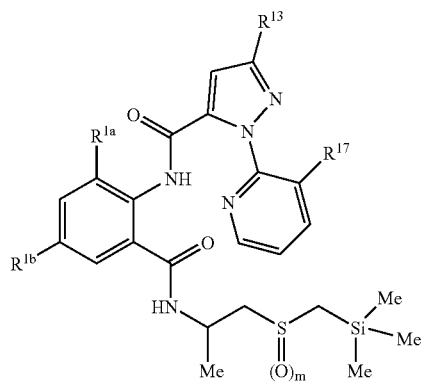

| $R^{1a}$ | $R^{1b}$ | $R^{13}$ | $R^{17}$ | m | $R^{1a}$ | $R^{1b}$ | $R^{13}$ | $R^{17}$ | m |
|---|---|---|---|---|---|---|---|---|---|
| Me | Cl | Cl | Cl | 0 | Me | Cl | Cl | Cl | 1 |
| Me | Br | Cl | Cl | 0 | Me | Br | Cl | Cl | 1 |
| Me | F | Cl | Cl | 0 | Me | F | Cl | Cl | 1 |
| Me | I | Cl | Cl | 0 | Me | I | Cl | Cl | 1 |
| Me | CN | Cl | Cl | 0 | Me | CN | Cl | Cl | 1 |
| Cl | Cl | Cl | Cl | 0 | Cl | Cl | Cl | Cl | 1 |
| Cl | Br | Cl | Cl | 0 | Cl | Br | Cl | Cl | 1 |
| Cl | F | Cl | Cl | 0 | Cl | F | Cl | Cl | 1 |
| Cl | I | Cl | Cl | 0 | Cl | I | Cl | Cl | 1 |
| Cl | CN | Cl | Cl | 0 | Cl | CN | Cl | Cl | 1 |
| Br | Cl | Cl | Cl | 0 | Br | Cl | Cl | Cl | 1 |
| Br | Br | Cl | Cl | 0 | Br | Br | Cl | Cl | 1 |
| Br | F | Cl | Cl | 0 | Br | F | Cl | Cl | 1 |
| Br | I | Cl | Cl | 0 | Br | I | Cl | Cl | 1 |
| Br | CN | Cl | Cl | 0 | Br | CN | Cl | Cl | 1 |
| Me | Cl | Br | Cl | 0 | Me | Cl | Br | Cl | 1 |
| Me | Br | Br | Cl | 0 | Me | Br | Br | Cl | 1 |
| Me | F | Br | Cl | 0 | Me | F | Br | Cl | 1 |
| Me | I | Br | Cl | 0 | Me | I | Br | Cl | 1 |
| Me | CN | Br | Cl | 0 | Me | CN | Br | Cl | 1 |
| Cl | Cl | Br | Cl | 0 | Cl | Cl | Br | Cl | 1 |
| Cl | Br | Br | Cl | 0 | Cl | Br | Br | Cl | I |
| Cl | F | Br | Cl | 0 | Cl | F | Br | Cl | 1 |
| Cl | I | Br | Cl | 0 | Cl | I | Br | Cl | 1 |
| Cl | CN | Br | Cl | 0 | Cl | CN | Br | Cl | 1 |
| Br | Cl | Br | Cl | 0 | Br | Cl | Br | Cl | 1 |
| Br | Br | Br | Cl | 0 | Br | Br | Br | Cl | 1 |
| Br | F | Br | Cl | 0 | Br | F | Br | Cl | 1 |
| Br | I | Br | Cl | 0 | Br | I | Br | Cl | 1 |
| Br | CN | Br | Cl | 0 | Br | CN | Br | Cl | 1 |
| Me | Cl | CF$_3$ | Cl | 0 | Me | Cl | CF$_3$ | Cl | 1 |
| Me | Br | CF$_3$ | Cl | 0 | Me | Br | CF$_3$ | Cl | 1 |
| Me | F | CF$_3$ | Cl | 0 | Me | F | CF$_3$ | Cl | 1 |
| Me | I | CF$_3$ | Cl | 0 | Me | I | CF$_3$ | Cl | 1 |
| Me | CN | CF$_3$ | Cl | 0 | Me | CN | CF$_3$ | Cl | 1 |
| Cl | Cl | CF$_3$ | Cl | 0 | Cl | Cl | CF$_3$ | Cl | 1 |
| Cl | Br | CF$_3$ | Cl | 0 | Cl | Br | CF$_3$ | Cl | 1 |
| Cl | F | CF$_3$ | Cl | 0 | Cl | F | CF$_3$ | Cl | 1 |
| Cl | I | CF$_3$ | Cl | 0 | Cl | I | CF$_3$ | Cl | 1 |
| Cl | CN | CF$_3$ | Cl | 0 | Cl | CN | CF$_3$ | Cl | 1 |
| Br | Cl | CF$_3$ | Cl | 0 | Br | Cl | CF$_3$ | Cl | 1 |
| Br | Br | CF$_3$ | Cl | 0 | Br | Br | CF$_3$ | Cl | 1 |
| Br | F | CF$_3$ | Cl | 0 | Br | F | CF$_3$ | Cl | 1 |
| Br | I | CF$_3$ | Cl | 0 | Br | I | CF$_3$ | Cl | 1 |
| Br | CN | CF$_3$ | Cl | 0 | Br | CN | CF$_3$ | Cl | 1 |
| Me | Cl | OCHF$_2$ | Cl | 0 | Me | Cl | OCHF$_2$ | Cl | 1 |
| Me | Br | OCHF$_2$ | Cl | 0 | Me | Br | OCHF$_2$ | Cl | 1 |
| Me | F | OCHF$_2$ | Cl | 0 | Me | F | OCHF$_2$ | Cl | 1 |

TABLE 1-continued

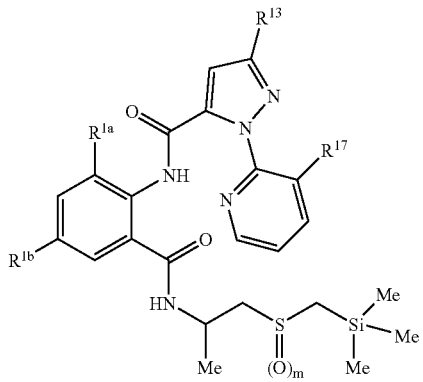

| R1a | R1b | R13 | R17 | m | R1a | R1b | R13 | R17 | m |
|---|---|---|---|---|---|---|---|---|---|
| Me | I | OCHF$_2$ | Cl | 0 | Me | I | OCHF$_2$ | Cl | 1 |
| Me | CN | OCHF$_2$ | Cl | 0 | Me | CN | OCHF$_2$ | Cl | 1 |
| Cl | Cl | OCHF$_2$ | Cl | 0 | Cl | Cl | OCHF$_2$ | Cl | 1 |
| Cl | Br | OCHF$_2$ | Cl | 0 | Cl | Br | OCHF$_2$ | Cl | 1 |
| Cl | F | OCHF$_2$ | Cl | 0 | Cl | F | OCHF$_2$ | Cl | 1 |
| Cl | I | OCHF$_2$ | Cl | 0 | Cl | I | OCHF$_2$ | Cl | 1 |
| Cl | CN | OCHF$_2$ | Cl | 0 | Cl | CN | OCHF$_2$ | Cl | 1 |
| Br | Cl | OCHF$_2$ | Cl | 0 | Br | Cl | OCHF$_2$ | Cl | 1 |
| Br | Br | OCHF$_2$ | Cl | 0 | Br | Br | OCHF$_2$ | Cl | 1 |
| Br | F | OCHF$_2$ | Cl | 0 | Br | F | OCHF$_2$ | Cl | 1 |
| Br | I | OCHF$_2$ | Cl | 0 | Br | I | OCHF$_2$ | Cl | 1 |
| Br | CN | OCHF$_2$ | Cl | 0 | Br | CN | OCHF$_2$ | Cl | 1 |
| Me | Cl | OCH$_2$CF$_3$ | Cl | 0 | Me | Cl | OCH$_2$CF$_3$ | Cl | 1 |
| Me | Br | OCH$_2$CF$_3$ | Cl | 0 | Me | Br | OCH$_2$CF$_3$ | Cl | 1 |
| Me | F | OCH$_2$CF$_3$ | Cl | 0 | Me | F | OCH$_2$CF$_3$ | Cl | 1 |
| Me | I | OCH$_2$CF$_3$ | Cl | 0 | Me | I | OCH$_2$CF$_3$ | Cl | 1 |
| Me | CN | OCH$_2$CF$_3$ | Cl | 0 | Me | CN | OCH$_2$CF$_3$ | Cl | 1 |
| Cl | Cl | OCH$_2$CF$_3$ | Cl | 0 | Cl | Cl | OCH$_2$CF$_3$ | Cl | 1 |
| Cl | Br | OCH$_2$CF$_3$ | Cl | 0 | Cl | Br | OCH$_2$CF$_3$ | Cl | 1 |
| Cl | F | OCH$_2$CF$_3$ | Cl | 0 | Cl | F | OCH$_2$CF$_3$ | Cl | 1 |
| Cl | I | OCH$_2$CF$_3$ | Cl | 0 | Cl | I | OCH$_2$CF$_3$ | Cl | 1 |
| Cl | CN | OCH$_2$CF$_3$ | Cl | 0 | Cl | CN | OCH$_2$CF$_3$ | Cl | 1 |
| Br | Cl | OCH$_2$CF$_3$ | Cl | 0 | Br | Cl | OCH$_2$CF$_3$ | Cl | 1 |
| Br | Br | OCH$_2$CF$_3$ | Cl | 0 | Br | Br | OCH$_2$CF$_3$ | Cl | 1 |
| Br | F | OCH$_2$CF$_3$ | Cl | 0 | Br | F | OCH$_2$CF$_3$ | Cl | 1 |
| Br | I | OCH$_2$CF$_3$ | Cl | 0 | Br | I | OCH$_2$CF$_3$ | Cl | 1 |
| Br | CN | OCH$_2$CF$_3$ | Cl | 0 | Br | CN | OCH$_2$CF$_3$ | Cl | 1 |
| Me | Cl | Cl | Br | 0 | Me | Cl | Cl | Br | 1 |
| Me | Cl | Cl | Cl | 2 | Me | Cl | CF$_3$ | Cl | 2 |
| Me | Br | Cl | Cl | 2 | Me | Br | CF$_3$ | Cl | 2 |
| Me | F | Cl | Cl | 2 | Me | F | CF$_3$ | Cl | 2 |
| Me | I | Cl | Cl | 2 | Me | I | CF$_3$ | Cl | 2 |
| Me | CN | Cl | Cl | 2 | Me | CN | CF$_3$ | Cl | 2 |
| Cl | Cl | Cl | Cl | 2 | Cl | Cl | CF$_3$ | Cl | 2 |
| Cl | Br | Cl | Cl | 2 | Cl | Br | CF$_3$ | Cl | 2 |
| Cl | F | Cl | Cl | 2 | Cl | F | CF$_3$ | Cl | 2 |
| Cl | I | Cl | Cl | 2 | Cl | I | CF$_3$ | Cl | 2 |
| Cl | CN | Cl | Cl | 2 | Cl | CN | CF$_3$ | Cl | 2 |
| Br | Cl | Cl | Cl | 2 | Br | Cl | CF$_3$ | Cl | 2 |
| Br | Br | Cl | Cl | 2 | Br | Br | CF$_3$ | Cl | 2 |
| Br | F | Cl | Cl | 2 | Br | F | CF$_3$ | Cl | 2 |
| Br | I | Cl | Cl | 2 | Br | I | CF$_3$ | Cl | 2 |
| Br | CN | Cl | Cl | 2 | Br | CN | CF$_3$ | Cl | 2 |
| Me | Cl | Br | Cl | 2 | Me | Cl | OCHF$_2$ | Cl | 2 |
| Me | Br | Br | Cl | 2 | Me | Br | OCHF$_2$ | Cl | 2 |
| Me | F | Br | Cl | 2 | Me | F | OCHF$_2$ | Cl | 2 |
| Me | I | Br | Cl | 2 | Me | I | OCHF$_2$ | Cl | 2 |
| Me | CN | Br | Cl | 2 | Me | CN | OCHF$_2$ | Cl | 2 |
| Cl | Cl | Br | Cl | 2 | Cl | Cl | OCHF$_2$ | Cl | 2 |
| Cl | Br | Br | Cl | 2 | Cl | Br | OCHF$_2$ | Cl | 2 |
| Cl | F | Br | Cl | 2 | Cl | F | OCHF$_2$ | Cl | 2 |
| Cl | I | Br | Cl | 2 | Cl | I | OCHF$_2$ | Cl | 2 |
| Cl | CN | Br | Cl | 2 | Cl | CN | OCHF$_2$ | Cl | 2 |
| Br | Cl | Br | Cl | 2 | Br | Cl | OCHF$_2$ | Cl | 2 |
| Br | Br | Br | Cl | 2 | Br | Br | OCHF$_2$ | Cl | 2 |
| Br | F | Br | Cl | 2 | Br | F | OCHF$_2$ | Cl | 2 |
| Br | I | Br | Cl | 2 | Br | I | OCHF$_2$ | Cl | 2 |
| Br | CN | Br | Cl | 2 | Br | CN | OCHF$_2$ | Cl | 2 |

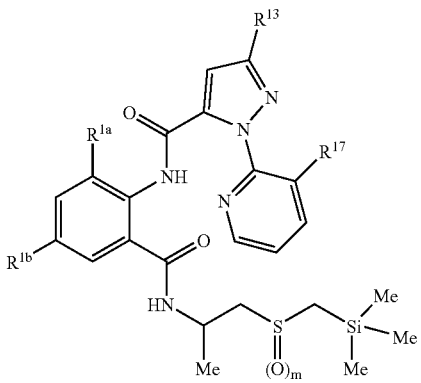

| R1a | R1b | R13 | R17 | m | R1a | R1b | R13 | R17 | m |
|---|---|---|---|---|---|---|---|---|---|
| Me | Cl | OCH$_2$CF$_3$ | Cl | 2 | Cl | Cl | OCH$_2$CF$_3$ | Cl | 2 |
| Me | Br | OCH$_2$CF$_3$ | Cl | 2 | Cl | Br | OCH$_2$CF$_3$ | Cl | 2 |
| Me | F | OCH$_2$CF$_3$ | Cl | 2 | Cl | F | OCH$_2$CF$_3$ | Cl | 2 |
| Me | I | OCH$_2$CF$_3$ | Cl | 2 | Cl | I | OCH$_2$CF$_3$ | Cl | 2 |
| Me | CN | OCH$_2$CF$_3$ | Cl | 2 | Cl | CN | OCH$_2$CF$_3$ | Cl | 2 |
| Br | Cl | OCH$_2$CF$_3$ | Cl | 2 | Br | I | OCH$_2$CF$_3$ | Cl | 2 |
| Br | Br | OCH$_2$CF$_3$ | Cl | 2 | Br | CN | OCH$_2$CF$_3$ | Cl | 2 |
| Br | F | OCH$_2$CF$_3$ | Cl | 2 | | | | | |

TABLE 2

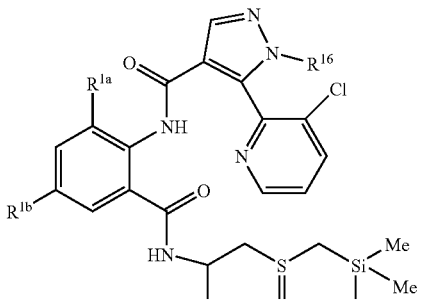

| R1a | R1b | R16 | m | R1a | R1b | R16 | m |
|---|---|---|---|---|---|---|---|
| Me | Cl | CHF$_2$ | 0 | Me | Cl | CHF$_2$ | 1 |
| Me | Br | CHF$_2$ | 0 | Me | Br | CHF$_2$ | 1 |
| Me | F | CHF$_2$ | 0 | Me | F | CHF$_2$ | 1 |
| Me | I | CHF$_2$ | 0 | Me | I | CHF$_2$ | 1 |
| Me | CN | CHF$_2$ | 0 | Me | CN | CHF$_2$ | 1 |
| Cl | Cl | CHF$_2$ | 0 | Cl | Cl | CHF$_2$ | 1 |
| Cl | Br | CHF$_2$ | 0 | Cl | Br | CHF$_2$ | 1 |
| Cl | F | CHF$_2$ | 0 | Cl | F | CHF$_2$ | 1 |
| Cl | I | CHF$_2$ | 0 | Cl | I | CHF$_2$ | 1 |
| Cl | CN | CHF$_2$ | 0 | Cl | CN | CHF$_2$ | 1 |
| Br | Cl | CHF$_2$ | 0 | Br | Cl | CHF$_2$ | 1 |
| Br | Br | CHF$_2$ | 0 | Br | Br | CHF$_2$ | 1 |
| Br | F | CHF$_2$ | 0 | Br | F | CHF$_2$ | 1 |
| Br | I | CHF$_2$ | 0 | Br | I | CHF$_2$ | 1 |
| Br | CN | CHF$_2$ | 0 | Br | CN | CHF$_2$ | 1 |
| Me | Cl | CH$_2$CF$_3$ | 0 | Me | Cl | CH$_2$CF$_3$ | 1 |
| Me | Br | CH$_2$CF$_3$ | 0 | Me | Br | CH$_2$CF$_3$ | 1 |
| Me | F | CH$_2$CF$_3$ | 0 | Me | F | CH$_2$CF$_3$ | 1 |
| Me | I | CH$_2$CF$_3$ | 0 | Me | I | CH$_2$CF$_3$ | 1 |
| Me | CN | CH$_2$CF$_3$ | 0 | Me | CN | CH$_2$CF$_3$ | 1 |
| Cl | Cl | CH$_2$CF$_3$ | 0 | Cl | Cl | CH$_2$CF$_3$ | 1 |
| Cl | Br | CH$_2$CF$_3$ | 0 | Cl | Br | CH$_2$CF$_3$ | 1 |
| Cl | F | CH$_2$CF$_3$ | 0 | Cl | F | CH$_2$CF$_3$ | 1 |
| Cl | I | CH$_2$CF$_3$ | 0 | Cl | I | CH$_2$CF$_3$ | 1 |
| Cl | CN | CH$_2$CF$_3$ | 0 | Cl | CN | CH$_2$CF$_3$ | 1 |
| Br | Cl | CH$_2$CF$_3$ | 0 | Br | Cl | CH$_2$CF$_3$ | 1 |

TABLE 2-continued

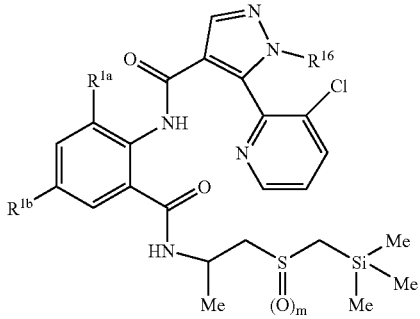

| R¹ᵃ | R¹ᵇ | R¹⁶ | m | R¹ᵃ | R¹ᵇ | R¹⁶ | m |
|---|---|---|---|---|---|---|---|
| Br | Br | CH₂CF₃ | 0 | Br | Br | CH₂CF₃ | 1 |
| Br | F | CH₂CF₃ | 0 | Br | F | CH₂CF₃ | 1 |
| Br | I | CH₂CF₃ | 0 | Br | I | CH₂CF₃ | 1 |
| Br | CN | CH₂CF₃ | 0 | Br | CN | CH₂CF₃ | 1 |
| Me | Cl | CHF₂ | 2 | Me | Cl | CH₂CF₃ | 2 |
| Me | Br | CHF₂ | 2 | Me | Br | CH₂CF₃ | 2 |
| Me | F | CHF₂ | 2 | Me | F | CH₂CF₃ | 2 |
| Me | I | CHF₂ | 2 | Me | I | CH₂CF₃ | 2 |
| Me | CN | CHF₂ | 2 | Me | CN | CH₂CF₃ | 2 |
| Cl | Cl | CHF₂ | 2 | Cl | Cl | CH₂CF₃ | 2 |
| Cl | Br | CHF₂ | 2 | Cl | Br | CH₂CF₃ | 2 |
| Cl | F | CHF₂ | 2 | Cl | F | CH₂CF₃ | 2 |
| Cl | I | CHF₂ | 2 | Cl | I | CH₂CF₃ | 2 |
| Cl | CN | CHF₂ | 2 | Cl | CN | CH₂CF₃ | 2 |
| Br | Cl | CHF₂ | 2 | Br | Cl | CH₂CF₃ | 2 |
| Br | Br | CHF₂ | 2 | Br | Br | CH₂CF₃ | 2 |
| Br | F | CHF₂ | 2 | Br | F | CH₂CF₃ | 2 |
| Br | I | CHF₂ | 2 | Br | I | CH₂CF₃ | 2 |
| Br | CN | CHF₂ | 2 | Br | CN | CH₂CF₃ | 2 |

TABLE 3

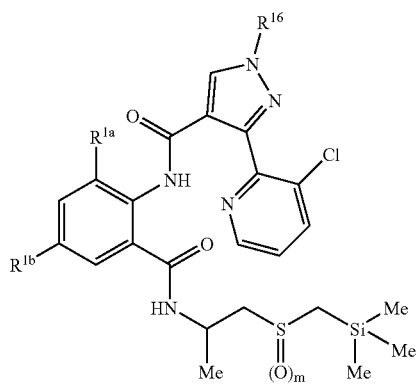

| R¹ᵃ | R¹ᵇ | R¹⁶ | m | R¹ᵃ | R¹ᵇ | R¹⁶ | m |
|---|---|---|---|---|---|---|---|
| Me | Cl | CHF₂ | 0 | Me | Cl | CHF₂ | 1 |
| Me | Br | CHF₂ | 0 | Me | Br | CHF₂ | 1 |
| Me | F | CHF₂ | 0 | Me | F | CHF₂ | 1 |
| Me | I | CHF₂ | 0 | Me | I | CHF₂ | 1 |
| Me | CN | CHF₂ | 0 | Me | CN | CHF₂ | 1 |
| Cl | Cl | CHF₂ | 0 | Cl | Cl | CHF₂ | 1 |
| Cl | Br | CHF₂ | 0 | Cl | Br | CHF₂ | 1 |
| Cl | F | CHF₂ | 0 | Cl | F | CHF₂ | 1 |
| Cl | I | CHF₂ | 0 | Cl | I | CHF₂ | 1 |
| Cl | CN | CHF₂ | 0 | Cl | CN | CHF₂ | 1 |
| Br | Cl | CHF₂ | 0 | Br | Cl | CHF₂ | 1 |
| Br | Br | CHF₂ | 0 | Br | Br | CHF₂ | 1 |
| Br | F | CHF₂ | 0 | Br | F | CHF₂ | 1 |
| Br | I | CHF₂ | 0 | Br | I | CHF₂ | 1 |
| Br | CN | CHF₂ | 0 | Br | CN | CHF₂ | 1 |

TABLE 3-continued

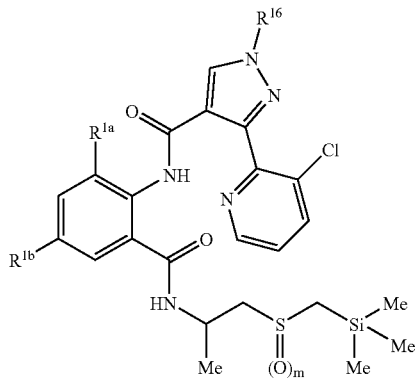

| R¹ᵃ | R¹ᵇ | R¹⁶ | m | R¹ᵃ | R¹ᵇ | R¹⁶ | m |
|---|---|---|---|---|---|---|---|
| Me | Cl | CH₂CF₃ | 0 | Me | Cl | CH₂CF₃ | 1 |
| Me | Br | CH₂CF₃ | 0 | Me | Br | CH₂CF₃ | 1 |
| Me | F | CH₂CF₃ | 0 | Me | F | CH₂CF₃ | 1 |
| Me | I | CH₂CF₃ | 0 | Me | I | CH₂CF₃ | 1 |
| Me | CN | CH₂CF₃ | 0 | Me | CN | CH₂CF₃ | 1 |
| Cl | Cl | CH₂CF₃ | 0 | Cl | Cl | CH₂CF₃ | 1 |
| Cl | Br | CH₂CF₃ | 0 | Cl | Br | CH₂CF₃ | 1 |
| Cl | F | CH₂CF₃ | 0 | Cl | F | CH₂CF₃ | 1 |
| Cl | I | CH₂CF₃ | 0 | Cl | I | CH₂CF₃ | 1 |
| Cl | CN | CH₂CF₃ | 0 | Cl | CN | CH₂CF₃ | 1 |
| Br | Cl | CH₂CF₃ | 0 | Br | Cl | CH₂CF₃ | 1 |
| Br | Br | CH₂CF₃ | 0 | Br | Br | CH₂CF₃ | 1 |
| Br | F | CH₂CF₃ | 0 | Br | F | CH₂CF₃ | 1 |
| Br | I | CH₂CF₃ | 0 | Br | I | CH₂CF₃ | 1 |
| Br | CN | CH₂CF₃ | 0 | Br | CN | CH₂CF₃ | 1 |
| Me | Cl | CHF₂ | 2 | Me | Cl | CH₂CF₃ | 2 |
| Me | Br | CHF₂ | 2 | Me | Br | CH₂CF₃ | 2 |
| Me | F | CHF₂ | 2 | Me | F | CH₂CF₃ | 2 |
| Me | I | CHF₂ | 2 | Me | I | CH₂CF₃ | 2 |
| Me | CN | CHF₂ | 2 | Me | CN | CH₂CF₃ | 2 |
| Cl | Cl | CHF₂ | 2 | Cl | Cl | CH₂CF₃ | 2 |
| Cl | Br | CHF₂ | 2 | Cl | Br | CH₂CF₃ | 2 |
| Cl | F | CHF₂ | 2 | Cl | F | CH₂CF₃ | 2 |
| Cl | I | CHF₂ | 2 | Cl | I | CH₂CF₃ | 2 |
| Cl | CN | CHF₂ | 2 | Cl | CN | CH₂CF₃ | 2 |
| Br | Cl | CHF₂ | 2 | Br | Cl | CH₂CF₃ | 2 |
| Br | Br | CHF₂ | 2 | Br | Br | CH₂CF₃ | 2 |
| Br | F | CHF₂ | 2 | Br | F | CH₂CF₃ | 2 |
| Br | I | CHF₂ | 2 | Br | I | CH₂CF₃ | 2 |
| Br | CN | CHF₂ | 2 | Br | CN | CH₂CF₃ | 2 |

TABLE 4

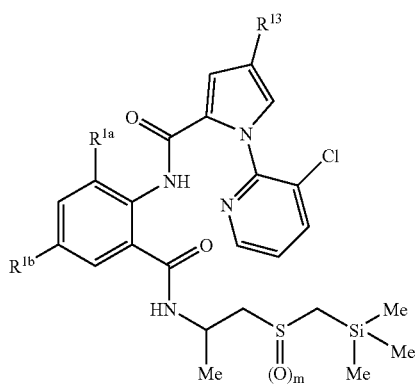

| R¹ᵃ | R¹ᵇ | R¹³ | m | R¹ᵃ | R¹ᵇ | R¹³ | m |
|---|---|---|---|---|---|---|---|
| Me | Cl | Cl | 0 | Me | Cl | Cl | 1 |
| Me | Br | Cl | 0 | Me | Br | Cl | 1 |

TABLE 4-continued

| $R^{1a}$ | $R^{1b}$ | $R^{13}$ | m | $R^{1a}$ | $R^{1b}$ | $R^{13}$ | m |
|---|---|---|---|---|---|---|---|
| Me | F | Cl | 0 | Me | F | Cl | 1 |
| Me | I | Cl | 0 | Me | I | Cl | 1 |
| Me | CN | Cl | 0 | Me | CN | Cl | 1 |
| Cl | Cl | Cl | 0 | Cl | Cl | Cl | 1 |
| Cl | Br | Cl | 0 | Cl | Br | Cl | 1 |
| Cl | F | Cl | 0 | Cl | F | Cl | 1 |
| Cl | I | Cl | 0 | Cl | I | Cl | 1 |
| Cl | CN | Cl | 0 | Cl | CN | Cl | 1 |
| Br | Cl | Cl | 0 | Br | Cl | Cl | 1 |
| Br | Br | Cl | 0 | Br | Br | Cl | 1 |
| Br | F | Cl | 0 | Br | F | Cl | 1 |
| Br | I | Cl | 0 | Br | I | Cl | 1 |
| Br | CN | Cl | 0 | Br | CN | Cl | 1 |
| Me | Cl | Br | 0 | Me | Cl | Br | 1 |
| Me | Br | Br | 0 | Me | Br | Br | 1 |
| Me | F | Br | 0 | Me | F | Br | 1 |
| Me | I | Br | 0 | Me | I | Br | 1 |
| Me | CN | Br | 0 | Me | CN | Br | 1 |
| Cl | Cl | Br | 0 | Cl | Cl | Br | 1 |
| Cl | Br | Br | 0 | Cl | Br | Br | 1 |
| Cl | F | Br | 0 | Cl | F | Br | 1 |
| Cl | I | Br | 0 | Cl | I | Br | 1 |
| Cl | CN | Br | 0 | Cl | CN | Br | 1 |
| Br | Cl | Br | 0 | Br | Cl | Br | 1 |
| Br | Br | Br | 0 | Br | Br | Br | 1 |
| Br | F | Br | 0 | Br | F | Br | 1 |
| Br | I | Br | 0 | Br | I | Br | 1 |
| Br | CN | Br | 0 | Br | CN | Br | 1 |
| Me | Cl | Cl | 2 | Me | Cl | Br | 2 |
| Me | Br | Cl | 2 | Me | Br | Br | 2 |
| Me | F | Cl | 2 | Me | F | Br | 2 |
| Me | I | Cl | 2 | Me | I | Br | 2 |
| Me | CN | Cl | 2 | Me | CN | Br | 2 |
| Cl | Cl | Cl | 2 | Cl | Cl | Br | 2 |
| Cl | Br | Cl | 2 | Cl | Br | Br | 2 |
| Cl | F | Cl | 2 | Cl | F | Br | 2 |
| Cl | I | Cl | 2 | Cl | I | Br | 2 |
| Cl | CN | Cl | 2 | Cl | CN | Br | 2 |
| Br | Cl | Cl | 2 | Br | Cl | Br | 2 |
| Br | Br | Cl | 2 | Br | Br | Br | 2 |
| Br | F | Cl | 2 | Br | F | Br | 2 |
| Br | I | Cl | 2 | Br | I | Br | 2 |
| Br | CN | Cl | 2 | Br | CN | Br | 2 |

TABLE 5

| $R^{1a}$ | $R^{1b}$ | $R^{16}$ | m | $R^{1a}$ | $R^{1b}$ | $R^{16}$ | m |
|---|---|---|---|---|---|---|---|
| Me | Cl | $CHF_2$ | 0 | Me | Cl | $CHF_2$ | 1 |
| Me | Br | $CHF_2$ | 0 | Me | Br | $CHF_2$ | 1 |
| Me | F | $CHF_2$ | 0 | Me | F | $CHF_2$ | 1 |
| Me | I | $CHF_2$ | 0 | Me | I | $CHF_2$ | 1 |
| Me | CN | $CHF_2$ | 0 | Me | CN | $CHF_2$ | 1 |
| Cl | Cl | $CHF_2$ | 0 | Cl | Cl | $CHF_2$ | 1 |
| Cl | Br | $CHF_2$ | 0 | Cl | Br | $CHF_2$ | 1 |
| Cl | F | $CHF_2$ | 0 | Cl | F | $CHF_2$ | 1 |
| Cl | I | $CHF_2$ | 0 | Cl | I | $CHF_2$ | 1 |
| Cl | CN | $CHF_2$ | 0 | Cl | CN | $CHF_2$ | 1 |
| Br | Cl | $CHF_2$ | 0 | Br | Cl | $CHF_2$ | 1 |
| Br | Br | $CHF_2$ | 0 | Br | Br | $CHF_2$ | 1 |
| Br | F | $CHF_2$ | 0 | Br | F | $CHF_2$ | 1 |
| Br | I | $CHF_2$ | 0 | Br | I | $CHF_2$ | 1 |
| Br | CN | $CHF_2$ | 0 | Br | CN | $CHF_2$ | 1 |
| Me | Cl | $CH_2CF_3$ | 0 | Me | Cl | $CH_2CF_3$ | 1 |
| Me | Br | $CH_2CF_3$ | 0 | Me | Br | $CH_2CF_3$ | 1 |
| Me | F | $CH_2CF_3$ | 0 | Me | F | $CH_2CF_3$ | 1 |
| Me | I | $CH_2CF_3$ | 0 | Me | I | $CH_2CF_3$ | 1 |
| Me | CN | $CH_2CF_3$ | 0 | Me | CN | $CH_2CF_3$ | 1 |
| Cl | Cl | $CH_2CF_3$ | 0 | Cl | Cl | $CH_2CF_3$ | 1 |
| Cl | Br | $CH_2CF_3$ | 0 | Cl | Br | $CH_2CF_3$ | 1 |
| Cl | F | $CH_2CF_3$ | 0 | Cl | F | $CH_2CF_3$ | 1 |
| Cl | I | $CH_2CF_3$ | 0 | Cl | I | $CH_2CF_3$ | 1 |
| Cl | CN | $CH_2CF_3$ | 0 | Cl | CN | $CH_2CF_3$ | 1 |
| Br | Cl | $CH_2CF_3$ | 0 | Br | Cl | $CH_2CF_3$ | 1 |
| Br | Br | $CH_2CF_3$ | 0 | Br | Br | $CH_2CF_3$ | 1 |
| Br | F | $CH_2CF_3$ | 0 | Br | F | $CH_2CF_3$ | 1 |
| Br | I | $CH_2CF_3$ | 0 | Br | I | $CH_2CF_3$ | 1 |
| Br | CN | $CH_2CF_3$ | 0 | Br | CN | $CH_2CF_3$ | 1 |
| Me | Cl | $CHF_2$ | 2 | Me | Cl | $CH_2CF_3$ | 2 |
| Me | Br | $CHF_2$ | 2 | Me | Br | $CH_2CF_3$ | 2 |
| Me | F | $CHF_2$ | 2 | Me | F | $CH_2CF_3$ | 2 |
| Me | I | $CHF_2$ | 2 | Me | I | $CH_2CF_3$ | 2 |
| Me | CN | $CHF_2$ | 2 | Me | CN | $CH_2CF_3$ | 2 |
| Cl | Cl | $CHF_2$ | 2 | Cl | Cl | $CH_2CF_3$ | 2 |
| Cl | Br | $CHF_2$ | 2 | Cl | Br | $CH_2CF_3$ | 2 |
| Cl | F | $CHF_2$ | 2 | Cl | F | $CH_2CF_3$ | 2 |
| Cl | I | $CHF_2$ | 2 | Cl | I | $CH_2CF_3$ | 2 |
| Cl | CN | $CHF_2$ | 2 | Cl | CN | $CH_2CF_3$ | 2 |
| Br | Cl | $CHF_2$ | 2 | Br | Cl | $CH_2CF_3$ | 2 |
| Br | Br | $CHF_2$ | 2 | Br | Br | $CH_2CF_3$ | 2 |
| Br | F | $CHF_2$ | 2 | Br | F | $CH_2CF_3$ | 2 |
| Br | I | $CHF_2$ | 2 | Br | I | $CH_2CF_3$ | 2 |
| Br | CN | $CHF_2$ | 2 | Br | CN | $CH_2CF_3$ | 2 |

TABLE 6

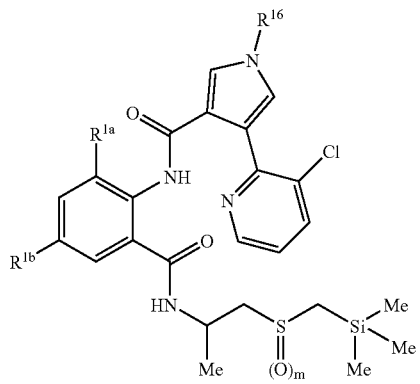

| $R^{1a}$ | $R^{1b}$ | $R^{16}$ | m | $R^{1a}$ | $R^{1b}$ | $R^{16}$ | m |
|---|---|---|---|---|---|---|---|
| Me | Cl | $CHF_2$ | 0 | Me | Cl | $CHF_2$ | 1 |
| Me | Br | $CHF_2$ | 0 | Me | Br | $CHF_2$ | 1 |
| Me | F | $CHF_2$ | 0 | Me | F | $CHF_2$ | 1 |
| Me | I | $CHF_2$ | 0 | Me | I | $CHF_2$ | 1 |
| Me | CN | $CHF_2$ | 0 | Me | CN | $CHF_2$ | 1 |
| Cl | Cl | $CHF_2$ | 0 | Cl | Cl | $CHF_2$ | 1 |
| Cl | Br | $CHF_2$ | 0 | Cl | Br | $CHF_2$ | 1 |
| Cl | F | $CHF_2$ | 0 | Cl | F | $CHF_2$ | 1 |
| Cl | I | $CHF_2$ | 0 | Cl | I | $CHF_2$ | 1 |
| Cl | CN | $CHF_2$ | 0 | Cl | CN | $CHF_2$ | 1 |
| Br | Cl | $CHF_2$ | 0 | Br | Cl | $CHF_2$ | 1 |
| Br | Br | $CHF_2$ | 0 | Br | Br | $CHF_2$ | 1 |
| Br | F | $CHF_2$ | 0 | Br | F | $CHF_2$ | 1 |
| Br | I | $CHF_2$ | 0 | Br | I | $CHF_2$ | 1 |
| Br | CN | $CHF_2$ | 0 | Br | CN | $CHF_2$ | 1 |
| Me | Cl | $CH_2CF_3$ | 0 | Me | Cl | $CH_2CF_3$ | 1 |
| Me | Br | $CH_2CF_3$ | 0 | Me | Br | $CH_2CF_3$ | 1 |
| Me | F | $CH_2CF_3$ | 0 | Me | F | $CH_2CF_3$ | 1 |
| Me | I | $CH_2CF_3$ | 0 | Me | I | $CH_2CF_3$ | 1 |
| Me | CN | $CH_2CF_3$ | 0 | Me | CN | $CH_2CF_3$ | 1 |
| Cl | Cl | $CH_2CF_3$ | 0 | Cl | Cl | $CH_2CF_3$ | 1 |
| Cl | Br | $CH_2CF_3$ | 0 | Cl | Br | $CH_2CF_3$ | 1 |
| Cl | F | $CH_2CF_3$ | 0 | Cl | F | $CH_2CF_3$ | 1 |
| Cl | I | $CH_2CF_3$ | 0 | Cl | I | $CH_2CF_3$ | 1 |
| Cl | CN | $CH_2CF_3$ | 0 | Cl | CN | $CH_2CF_3$ | 1 |
| Br | Cl | $CH_2CF_3$ | 0 | Br | Cl | $CH_2CF_3$ | 1 |
| Br | Br | $CH_2CF_3$ | 0 | Br | Br | $CH_2CF_3$ | 1 |
| Br | F | $CH_2CF_3$ | 0 | Br | F | $CH_2CF_3$ | 1 |
| Br | I | $CH_2CF_3$ | 0 | Br | I | $CH_2CF_3$ | 1 |
| Br | CN | $CH_2CF_3$ | 0 | Br | CN | $CH_2CF_3$ | 1 |
| Me | Cl | $CHF_2$ | 2 | Me | Cl | $CH_2CF_3$ | 2 |
| Me | Br | $CHF_2$ | 2 | Me | Br | $CH_2CF_3$ | 2 |
| Me | F | $CHF_2$ | 2 | Me | F | $CH_2CF_3$ | 2 |
| Me | I | $CHF_2$ | 2 | Me | I | $CH_2CF_3$ | 2 |
| Me | CN | $CHF_2$ | 2 | Me | CN | $CH_2CF_3$ | 2 |
| Cl | Cl | $CHF_2$ | 2 | Cl | Cl | $CH_2CF_3$ | 2 |
| Cl | Br | $CHF_2$ | 2 | Cl | Br | $CH_2CF_3$ | 2 |
| Cl | F | $CHF_2$ | 2 | Cl | F | $CH_2CF_3$ | 2 |
| Cl | I | $CHF_2$ | 2 | Cl | I | $CH_2CF_3$ | 2 |
| Cl | CN | $CHF_2$ | 2 | Cl | CN | $CH_2CF_3$ | 2 |
| Br | Cl | $CHF_2$ | 2 | Br | Cl | $CH_2CF_3$ | 2 |
| Br | Br | $CHF_2$ | 2 | Br | Br | $CH_2CF_3$ | 2 |
| Br | F | $CHF_2$ | 2 | Br | F | $CH_2CF_3$ | 2 |
| Br | I | $CHF_2$ | 2 | Br | I | $CH_2CF_3$ | 2 |
| Br | CN | $CHF_2$ | 2 | Br | CN | $CH_2CF_3$ | 2 |

TABLE 7

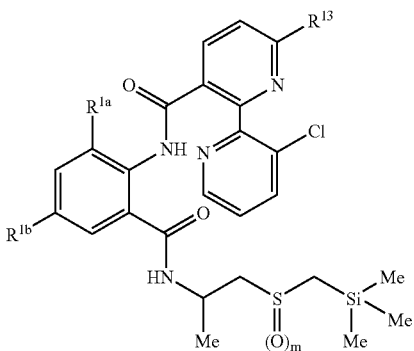

| $R^{1a}$ | $R^{1b}$ | $R^{13}$ | m | $R^{1a}$ | $R^{1b}$ | $R^{13}$ | m |
|---|---|---|---|---|---|---|---|
| Me | Cl | $CF_3$ | 0 | Me | Cl | $CF_3$ | 1 |
| Me | Br | $CF_3$ | 0 | Me | Br | $CF_3$ | 1 |
| Me | F | $CF_3$ | 0 | Me | F | $CF_3$ | 1 |
| Me | I | $CF_3$ | 0 | Me | I | $CF_3$ | 1 |
| Me | CN | $CF_3$ | 0 | Me | CN | $CF_3$ | 1 |
| Cl | Cl | $CF_3$ | 0 | Cl | Cl | $CF_3$ | 1 |
| Cl | Br | $CF_3$ | 0 | Cl | Br | $CF_3$ | 1 |
| Cl | F | $CF_3$ | 0 | Cl | F | $CF_3$ | 1 |
| Cl | I | $CF_3$ | 0 | Cl | I | $CF_3$ | 1 |
| Cl | CN | $CF_3$ | 0 | Cl | CN | $CF_3$ | 1 |
| Br | Cl | $CF_3$ | 0 | Br | Cl | $CF_3$ | 1 |
| Br | Br | $CF_3$ | 0 | Br | Br | $CF_3$ | 1 |
| Br | F | $CF_3$ | 0 | Br | F | $CF_3$ | 1 |
| Br | I | $CF_3$ | 0 | Br | I | $CF_3$ | 1 |
| Br | CN | $CF_3$ | 0 | Br | CN | $CF_3$ | 1 |
| Me | Cl | $CH_2CF_3$ | 0 | Me | Cl | $CH_2CF_3$ | 1 |
| Me | Br | $CH_2CF_3$ | 0 | Me | Br | $CH_2CF_3$ | 1 |
| Me | F | $CH_2CF_3$ | 0 | Me | F | $CH_2CF_3$ | 1 |
| Me | I | $CH_2CF_3$ | 0 | Me | I | $CH_2CF_3$ | 1 |
| Me | CN | $CH_2CF_3$ | 0 | Me | CN | $CH_2CF_3$ | 1 |
| Cl | Cl | $CH_2CF_3$ | 0 | Cl | Cl | $CH_2CF_3$ | 1 |
| Cl | Br | $CH_2CF_3$ | 0 | Cl | Br | $CH_2CF_3$ | 1 |
| Cl | F | $CH_2CF_3$ | 0 | Cl | F | $CH_2CF_3$ | 1 |
| Cl | I | $CH_2CF_3$ | 0 | Cl | I | $CH_2CF_3$ | 1 |
| Cl | CN | $CH_2CF_3$ | 0 | Cl | CN | $CH_2CF_3$ | 1 |
| Br | Cl | $CH_2CF_3$ | 0 | Br | Cl | $CH_2CF_3$ | 1 |
| Br | Br | $CH_2CF_3$ | 0 | Br | Br | $CH_2CF_3$ | 1 |
| Br | F | $CH_2CF_3$ | 0 | Br | F | $CH_2CF_3$ | 1 |
| Br | I | $CH_2CF_3$ | 0 | Br | I | $CH_2CF_3$ | 1 |
| Br | CN | $CH_2CF_3$ | 0 | Br | CN | $CH_2CF_3$ | 1 |
| Me | Cl | $CF_3$ | 2 | Me | Cl | $CH_2CF_3$ | 2 |
| Me | Br | $CF_3$ | 2 | Me | Br | $CH_2CF_3$ | 2 |
| Me | F | $CF_3$ | 2 | Me | F | $CH_2CF_3$ | 2 |
| Me | I | $CF_3$ | 2 | Me | I | $CH_2CF_3$ | 2 |
| Me | CN | $CF_3$ | 2 | Me | CN | $CH_2CF_3$ | 2 |
| Cl | Cl | $CF_3$ | 2 | Cl | Cl | $CH_2CF_3$ | 2 |
| Cl | Br | $CF_3$ | 2 | Cl | Br | $CH_2CF_3$ | 2 |
| Cl | F | $CF_3$ | 2 | Cl | F | $CH_2CF_3$ | 2 |
| Cl | I | $CF_3$ | 2 | Cl | I | $CH_2CF_3$ | 2 |
| Cl | CN | $CF_3$ | 2 | Cl | CN | $CH_2CF_3$ | 2 |
| Br | Cl | $CF_3$ | 2 | Br | Cl | $CH_2CF_3$ | 2 |
| Br | Br | $CF_3$ | 2 | Br | Br | $CH_2CF_3$ | 2 |
| Br | F | $CF_3$ | 2 | Br | F | $CH_2CF_3$ | 2 |
| Br | I | $CF_3$ | 2 | Br | I | $CH_2CF_3$ | 2 |
| Br | CN | $CF_3$ | 2 | Br | CN | $CH_2CF_3$ | 2 |

TABLE 8

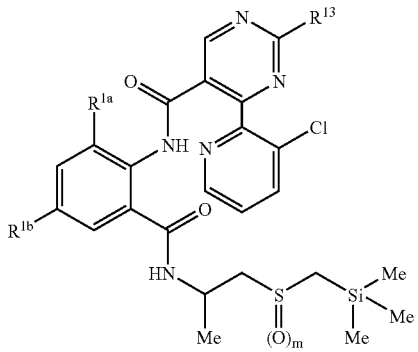

| $R^{1a}$ | $R^{1b}$ | $R^{13}$ | m | $R^{1a}$ | $R^{1b}$ | $R^{13}$ | m |
|---|---|---|---|---|---|---|---|
| Me | Cl | $CHF_2$ | 0 | Me | Cl | $CHF_2$ | 1 |
| Me | Br | $CHF_2$ | 0 | Me | Br | $CHF_2$ | 1 |
| Me | F | $CHF_2$ | 0 | Me | F | $CHF_2$ | 1 |
| Me | I | $CHF_2$ | 0 | Me | I | $CHF_2$ | 1 |
| Me | CN | $CHF_2$ | 0 | Me | CN | $CHF_2$ | 1 |
| Cl | Cl | $CHF_2$ | 0 | Cl | Cl | $CHF_2$ | 1 |
| Cl | Br | $CHF_2$ | 0 | Cl | Br | $CHF_2$ | 1 |
| Cl | F | $CHF_2$ | 0 | Cl | F | $CHF_2$ | 1 |
| Cl | I | $CHF_2$ | 0 | Cl | I | $CHF_2$ | 1 |
| Cl | CN | $CHF_2$ | 0 | Cl | CN | $CHF_2$ | 1 |
| Br | Cl | $CHF_2$ | 0 | Br | Cl | $CHF_2$ | 1 |
| Br | Br | $CHF_2$ | 0 | Br | Br | $CHF_2$ | 1 |
| Br | F | $CHF_2$ | 0 | Br | F | $CHF_2$ | 1 |
| Br | I | $CHF_2$ | 0 | Br | I | $CHF_2$ | 1 |
| Br | CN | $CHF_2$ | 0 | Br | CN | $CHF_2$ | 1 |
| Me | Cl | $CH_2CF_3$ | 0 | Me | Cl | $CH_2CF_3$ | 1 |
| Me | Br | $CH_2CF_3$ | 0 | Me | Br | $CH_2CF_3$ | 1 |
| Me | F | $CH_2CF_3$ | 0 | Me | F | $CH_2CF_3$ | 1 |
| Me | I | $CH_2CF_3$ | 0 | Me | I | $CH_2CF_3$ | 1 |
| Me | CN | $CH_2CF_3$ | 0 | Me | CN | $CH_2CF_3$ | 1 |
| Cl | Cl | $CH_2CF_3$ | 0 | Cl | Cl | $CH_2CF_3$ | 1 |
| Cl | Br | $CH_2CF_3$ | 0 | Cl | Br | $CH_2CF_3$ | 1 |
| Cl | F | $CH_2CF_3$ | 0 | Cl | F | $CH_2CF_3$ | 1 |
| Cl | I | $CH_2CF_3$ | 0 | Cl | I | $CH_2CF_3$ | 1 |
| Cl | CN | $CH_2CF_3$ | 0 | Cl | CN | $CH_2CF_3$ | 1 |
| Br | Cl | $CH_2CF_3$ | 0 | Br | Cl | $CH_2CF_3$ | 1 |
| Br | Br | $CH_2CF_3$ | 0 | Br | Br | $CH_2CF_3$ | 1 |
| Br | F | $CH_2CF_3$ | 0 | Br | F | $CH_2CF_3$ | 1 |
| Br | I | $CH_2CF_3$ | 0 | Br | I | $CH_2CF_3$ | 1 |
| Br | CN | $CH_2CF_3$ | 0 | Br | CN | $CH_2CF_3$ | 1 |
| Me | Cl | $CHF_2$ | 2 | Me | Cl | $CH_2CF_3$ | 2 |
| Me | Br | $CHF_2$ | 2 | Me | Br | $CH_2CF_3$ | 2 |
| Me | F | $CHF_2$ | 2 | Me | F | $CH_2CF_3$ | 2 |
| Me | I | $CHF_2$ | 2 | Me | I | $CH_2CF_3$ | 2 |
| Me | CN | $CHF_2$ | 2 | Me | CN | $CH_2CF_3$ | 2 |
| Cl | Cl | $CHF_2$ | 2 | Cl | Cl | $CH_2CF_3$ | 2 |
| Cl | Br | $CHF_2$ | 2 | Cl | Br | $CH_2CF_3$ | 2 |
| Cl | F | $CHF_2$ | 2 | Cl | F | $CH_2CF_3$ | 2 |
| Cl | I | $CHF_2$ | 2 | Cl | I | $CH_2CF_3$ | 2 |
| Cl | CN | $CHF_2$ | 2 | Cl | CN | $CH_2CF_3$ | 2 |
| Br | Cl | $CHF_2$ | 2 | Br | Cl | $CH_2CF_3$ | 2 |
| Br | Br | $CHF_2$ | 2 | Br | Br | $CH_2CF_3$ | 2 |
| Br | F | $CHF_2$ | 2 | Br | F | $CH_2CF_3$ | 2 |
| Br | I | $CHF_2$ | 2 | Br | I | $CH_2CF_3$ | 2 |
| Br | CN | $CHF_2$ | 2 | Br | CN | $CH_2CF_3$ | 2 |

Formulation/Utility

Compounds of this invention will generally be used as a formulation or composition with a carrier suitable for agronomic or nonagronomic use comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges that add up to 100 percent by weight.

|  | Weight Percent | | |
|---|---|---|---|
|  | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No.

3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and PCT Publication WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Enivironment Challenge*, T. Brooks and T. R. Roberts, Eds., Proceedings of the 9th International Congress on Pesticide Chemistry, The Royal Society of Chemistry, Cambridge, 1999, pp. 120–133. See also U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Table A.

EXAMPLE A

| Wettable Powder | |
| --- | --- |
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

EXAMPLE B

| Granule | |
| --- | --- |
| Compound 1 | 10.0% |
| attapulgite granules (low volatile matter, 0.71/0.30 mm; U.S.S. No. 25–50 sieves) | 90.0%. |

EXAMPLE C

Extruded Pellet

| Extruded Pellet | |
| --- | --- |
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

EXAMPLE D

Emulsifiable Concentrate

| Emulsifiable Concentrate | |
| --- | --- |
| Compound 1 | 20.0% |
| blend of oil soluble sulfonates and polyoxyethylene ethers | 10.0% |
| isophorone | 70.0%. |

EXAMPLE E

Granule

| Granule | |
| --- | --- |
| Compound 1 | 0.5% |
| cellulose | 2.5% |
| lactose | 4.0% |
| cornmeal | 93.0%. |

Compounds of this invention are characterized by favorable metabolic and/or soil residual patterns and exhibit activity controlling a spectrum of agronomic and nonagronomic invertebrate pests. (In the context of this disclosure "invertebrate pest control" means inhibition of invertebrate pest development (including mortality) that causes significant reduction in feeding or other injury or damage caused by the pest; related expressions are defined analogously.) As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda). Those skilled in the art will recognize that not all compounds are equally effective against all pests. Compounds of this invention display activity against economically important agronomic and nonagronomic pests. The term "agronomic" refers to the production of field crops such as for food and fiber and includes the growth of cereal crops (e.g., wheat, oats, barley, rye, rice, maize), soybeans, vegetable crops (e.g., lettuce, cabbage, tomatoes, beans), potatoes, sweet potatoes, grapes, cotton, and tree fruits (e.g., pome fruits, stone fruits and citrus fruits). The term "nonagronomic" refers to other horticultural (e.g., forest, greenhouse, nursery or ornamental plants not grown in a field), public (human) and animal health, domestic and commercial structure, household, and stored product applications or pests. For reason of invertebrate pest control spectrum and economic importance, protection (from damage or injury caused by invertebrate pests) of agronomic crops of cotton, maize, soybeans, rice, vegetable crops, potato, sweet potato, grapes and tree fruit by controlling invertebrate pests are preferred embodiments of the invention. Agronomic or nonagronomic pests include larvae of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua*

Hübner), black cutworm (*Agrotis ipsilon* Hufnagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworm (*Herpetogramina licarsisalis* Walker)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella gennanzica* Linnaeus), brownbanded cockroach (*Supella longipalpa* Fabricius), American cockroach (*Periplanieta americana* Linnaeus), brown cockroach (*Periplaizeta brunnea* Burmeister), Madeira cockroach (*Leucophaea maderae* Fabricius)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scarabaeidae (e.g., Japanese beetle (*Popillia japonica* Newman) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition agronomic and nonagronomic pests include: adults and larvae of the order Dermaptera including earwigs from the family Forficulidae (e.g., European earwig (*Forficula auricularia* Linnaeus), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae. Also included are adults and larvae of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)), flat mites in the family Tenuipalpidae (e.g., citrus flat mite (*Brevipalpus lewisi* McGregor)), rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Pabricius, *M. differentialis* Thomas), American grasshoppers (e.g., *Schistocerca americana* Drury), desert locust (*Schistocerca gregaria* Forskal), migratory locust (*Locusta migratoria* Linnaeus), house cricket (*Acheta domesticus* Linnaeus), mole crickets (*Gryllotalpa* spp.)); adults and immatures of the order Diptera including leafminers, midges, fruit flies (Tephritidae), frit flies (e.g., *Oscinella frit* Linnaeus), soil maggots, house flies (e.g., *Musca doinestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phonnia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman) and other foliar feeding thrips; insect pests of the order Hymenoptera including ants (e.g., red carpenter ant (*Camponotus ferrugineus* Pabricius), black carpenter ant (*Camponotus pennsylvanicus* De Geer), Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster), odorous house ant (*Tapinoma sessile* Say)), bees (including carpenter bees), hornets, yellow jackets and wasps; insect pests of the order Isoptera including eastern subterranean termite (*Reticulitermes flavipes* Kollar), western subterranean termite (*Reticuliternes hesperus* Banks), Formosan subterranean termite (*Coptotermes formosanus* Shiraki), West Indian drywood termite (*Incisitermes immigrans* Snyder) and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus humanus* Linnaeus), chicken body louse (*Menacanthus strainineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds.

Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus). Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenee (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)). Compounds of the invention also have commercially significant activity on members from the order Homoptera including: *Acyrthisiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosipum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (nglish grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla). These compounds also have activity on members from the order Hemiptera including: *Acrosternuin hilare* Say (green stink bug), *Anasa tristis* De Geer (squash bug), *Blissus leucopterus* leucopterus Say (chinch bug), *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrip), *Scirthothrips citri* Moulton (citrus thrip), *Sericothrips variabilis* Beach (soybean thrip), and *Thrips tabaci* Lindeman (onion thrip); and the order Coleoptera (e.g., *Leptinotarsa decemlineata* Say (Colorado potato beetle), *Epilachna varivestis* Mulsant (Mexican bean beetle) and wireworms of the genera *Agriotes*, *Athous* or *Limonius*).

Compounds of this invention can also be mixed with one or more other biologically active compounds or agents including insecticides, fungicides, nematocides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural utility. Thus compositions of the present invention can further comprise a biologically effective amount of at least one additional biologically active compound or agent. Examples of such biologically active compounds or agents with which compounds of this invention can be formulated are: insecticides such as abamectin, acephate, acetamiprid, avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, oxamyl, parathion, parathion-methyl, permethrin, phorate, phosalone, phosmet, phosphamidon, pirimicarb, profenofos, pymetrozine, pyridalyl, pyriproxyfen, rotenone, spinosad, sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenylamino)-4H-imdazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metominostrobin/fenominostrobin (SSF-126), myclobutanil, neo-asozin (ferric methanearsonate), oxadixyl, penconazole, pencycuron, probenazole, prochloraz, propamocarb, propiconazole, pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis* including ssp. *aizawai* and *kurstaki*, *Bacillus thuringiensis* delta endotoxin, baculovirus, and entomopathogenic bacteria, virus and fungi. Compounds of this invention and compositions thereof may be applied to plants genetically transformed to express proteins toxic to invertebrate pests (such as *Bacillus thuringiensis* toxin). The effect of the exogenous invertebrate pest control compounds and compositions may be synergistic with the expressed toxin proteins.

A general reference for these agricultural protectants is *The Pesticide Manual*, 12th Edition, C. D. S. Tomlin, Ed., British Crop Protection Council, Farnham, Surrey, U.K., 2000.

Preferred insecticides and acaricides for mixing with compounds of this invention include pyrethroids such as cypermethrin, cyhalothrin, cyfluthrin, beta-cyfluthrin, esfenvalerate, fenvalerate and tralomethrin; carbamates such as fenothicarb, methomyl, oxamyl and thiodicarb; neonicotinoids such as clothianidin, imidacloprid and thiacloprid; neuronal sodium channel blockers such as indoxacarb; insecticidal macrocyclic lactones such as spinosad, abamectin, avermectin and emamectin; γ-aminobutyric acid (GABA) antagonists such as endosulfan, ethiprole and fipronil; insecticidal ureas such as flufenoxuron and triflumuron; juvenile hormone mimics such as diofenolan and pyriproxyfen; pymetrozine; and amitraz. Preferred biological agents for mixing with compounds of this invention include *Bacillus thuringiensis* and *Bacillus thuringiensis* delta endotoxin as well as naturally occurring and genetically modified viral insecticides including members of the family Baculoviridae as well as entomophagous fungi.

Most preferred mixtures include a mixture of a compound of this invention with cyhalothrin; a mixture of a compound of this invention with beta-cyfluthrin; a mixture of a compound of this invention with esfenvalerate; a mixture of a compound of this invention with methomyl; a mixture of a compound of this invention with imidacloprid; a mixture of a compound of this invention with thiacloprid; a mixture of a compound of this invention with indoxacarb; a mixture of a compound of this invention with abamectin; a mixture of a compound of this invention with endosulfan; a mixture of a compound of this invention with ethiprole; a mixture of a compound of this invention with fipronil; a mixture of a compound of this invention with flufenoxuron; a mixture of a compound of this invention with pyriproxyfen; a mixture of a compound of this invention with pymetrozine; a mixture of a compound of this invention with amitraz; a mixture of a compound of this invention with *Bacillus thuringiensis* and a mixture of a compound of this invention with *Bacillus thuringiensis* delta endotoxin.

In certain instances, combinations with other invertebrate-pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of invention can also provide a broader spectrum of plant protection and be advantageous for resistance management.

Invertebrate pests are controlled in agronomic and nonagronomic applications by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of invertebrates in agronomic and/or nonagronomic applications, comprising contacting the invertebrates or their environment with a biologically effective amount of one or more of the compounds of the invention, or with a composition comprising at least one such compound or a composition comprising at least one such compound and an effective amount of at least one additional biologically active compound or agent. Examples of suitable compositions comprising a compound of the invention and an effective amount of at least one additional biologically active compound or agent include granular compositions wherein the additional biologically active compound is present on the same granule as the compound of the invention or on granules separate from those of the compound of this invention.

A preferred method of contact is by spraying. Alternatively, a granular composition comprising a compound of the invention can be applied to the plant foliage or the soil. Compounds of this invention are also effectively delivered through plant uptake by contacting the plant with a composition comprising a compound of this invention applied as a soil drench of a liquid formulation, a granular formulation to the soil, a nursery box treatment or a dip of transplants. Compounds are also effective by topical application of a composition comprising a compound of this invention to the locus of infestation. Other methods of contact include application of a compound or a composition of the invention by direct and residual sprays, aerial sprays, gels, seed coatings, microencapsulations, systemic uptake, baits, eartags, boluses, foggers, fumigants, aerosols, dusts and many others. The compounds of this invention may also be impregnated into materials for fabricating invertebrate control devices (e.g. insect netting).

A compound of this invention can be incorporated into a bait composition that is consumed by an invertebrate pest or used within devices such as traps, bait stations, and the like. Such a bait composition can be in the form of granules which comprise (a) an active ingredient, namely a compound of Formula I, an N-oxide, or salt thereof, (b) one or more food materials, (c) optionally an attractant, and (d) optionally one or more humectants. Of note granules or bait compositions which comprise between about 0.001–5% active ingredient; about 40–99% food material and/or attractant; and optionally about 0.05–10% humectants; are effective in controlling soil invertebrate pests at very low application rates, particularly at doses of active ingredient that are lethal by ingestion rather than by direct contact. Of note some food materials will function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest. Examples of humectants, i.e. moisture retaining agents, are glycols and other polyols, glycerine and sorbitol. Of note is a bait composition (and a method utilizing such a bait composition) used to control invertebrate pests including individually or in combinations ants, termites, and cockroaches. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g. a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a compound or composition of the present invention and a propellant. Representative propellants include, but are not limited to, methane, ethane, propane, iospropane, butane, isobutane, butene, pentane, iospentane, neopentane, pentene, hydrofluorocarbons, chlorofluoroacarbons, dimethyl ether, and mixtures of the foregoing. Of note is a spray composition (and a method utilizing such a spray composition dispensed from a spray container) used to control an invertebrate pest including individually or in combinations mosquitoes, black flies, stable flies, deer flies, horse flies, wasps, yellow jackets, hornets, ticks, spiders, ants, gnats, and the like.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

The following TESTS demonstrate the control efficacy of compounds of this invention on specific pests. "Control efficacy" represents inhibition of invertebrate pest development (including mortality) that causes significantly reduced feeding. The pest control protection afforded by the compounds is not limited, however, to these species. See Index Table A for compound descriptions. The abbreviation "Me" in the Index Table is methyl. The abbreviation "Ex." stands for "Example" and is followed by a number indicating in which example the compound is prepared.

INDEX TABLE A

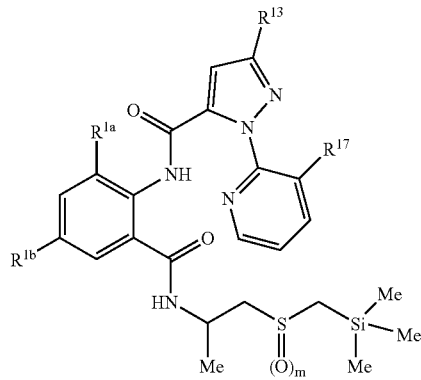

| Compound | $R^{1a}$ | $R^{1b}$ | $R^{13}$ | $R^{17}$ | m | m.p. ° C. |
|---|---|---|---|---|---|---|
| 1 (Ex. 1) | Me | Cl | Br | Cl | 0 | 151–153 |
| 2 | Cl | Cl | Br | Cl | 0 | 171–172 |
| 3 | Me | CN | $CF_3$ | Cl | 0 | 202–203 |
| 4 | Me | I | Br | Cl | 0 | 161–162 |
| 5 | Me | Cl | $CF_3$ | Cl | 0 | 152–153 |
| 6 | Me | Cl | $OCH_2CF_3$ | Cl | 0 | 151–152 |

BIOLOGICAL EXAMPLES OF THE INVENTION

Test A

For evaluating control of diamondback moth (*Plutella xylostella*) the test unit consisted of a small open container with a 12–14-day-old radish plant inside. This was pre-infested with 10–15 neonate larvae on a piece of insect diet by use of a core sampler to remove a plug from a sheet of hardened insect diet having many larvae growing on it and transfer the plug containing larvae and diet to the test unit. The larvae moved onto the test plant as the diet plug dried out.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc. Greeley, Colo., USA), unless otherwise indicated. The formulated compounds were applied in 1 mL of liquid through a SUJ2 atomizer nozzle with ⅛ JJ custom body (Spraying Systems Co. Wheaton, Ill., USA) positioned 1.27 cm (0.5 inches) above the top of each test unit. Test compounds 2, 3, 4, 5 and 6 were sprayed at 10 ppm and test compound 1 was sprayed at 50 ppm and all replicated three times. After spraying of the formulated test compound, each test unit was allowed to dry for 1 hour and then a black, screened cap was placed on top. The test units were held for 6 days in a growth chamber at 25° C. and 70% relative humidity. Plant feeding damage was then visually assessed based on foliage consumed.

Of the compounds tested the following provided very good to excellent levels of plant protection (20% or less feeding damage): 1, 2, 3, 4, 5 and 6.

Test B

For evaluating control of fall armyworm (*Spodoptera frugiperda*) the test unit consisted of a small open container with a 4–5-day-old corn (maize) plant inside. This was pre-infested (using a core sampler) with 10–15 1-day-old larvae on a piece of insect diet.

Test compounds 2, 3, 4, 5 and 6 were formulated and sprayed at 10 ppm and test compound 1 was formulated and sprayed at 50 ppm as described for Test A. The applications were replicated three times. After spraying, the test units were maintained in a growth chamber and then visually rated as described for Test A.

Of the compounds tested, the following provided excellent levels of plant protection (20% or less feeding damage): 1, 2, 3, 4, 5 and 6.

What is claimed:

1. A compound of Formula I, its N-oxide or suitable salts thereof

I

[Structure of Formula I: anthranilic diamide with substituents $(R_1)_n$ on benzene ring, $N(R^2)$-C(=O)-J group at position 2, and C(=O)-N($R^3$)-(CR$^4$R$^5$)-(CR$^6$R$^7$)-A-(CR$^8$R$^9$)$_r$-Si(R$^{10}$R$^{11}$R$^{12}$) group]

wherein:

A is O or S(O)$_m$;

J is a phenyl optionally substituted with one to four substituents independently selected from the group R$^{15}$; or J is a heterocyclic ring selected from the group consisting of J-1: pyrazole with R$^{13}$ at position 3, R$^{14}$ at N1

J-2: pyrazole with R$^{14}$ and R$^{16}$ substituents

J-3: pyrazole with R$^{16}$ at N1, R$^{14}$ substituent

J-4: pyrrole with R$^{13}$ at position 4, R$^{14}$ at N

J-5: pyrrole with R$^{16}$, R$^{14}$ substituents

J-6: pyrrole with R$^{16}$ at N, R$^{14}$ substituent

J-7: pyridine with R$^{13}$ and R$^{14}$ substituents, and

J-8: pyrimidine with R$^{13}$ and R$^{14}$ substituents each R$_1$ is independently selected from the group consisting of C$_1$–C$_6$ alkyl, C$_2$–C$_6$ alkenyl, C$_2$–C$_6$ alkynyl, C$_3$–C$_6$ cycloalkyl, C$_1$–C$_6$ haloalkyl, C$_2$–C$_6$ haloalkenyl, C$_2$–C$_6$ haloalkynyl, C$_3$–C$_6$ halocycloalkyl, halogen, CN, NO$_2$, hydroxy, C$_1$–C$_4$ alkoxy, C$_1$–C$_4$ haloalkoxy, C$_1$–C$_4$ alkylthio, C$_1$–C$_4$ alkylsulfinyl, C$_1$–C$_4$ alkylsulfonyl, $C_1$–$C_4$ haloalkylthio, $C_1$–$C_4$ haloalkylsulfinyl, $C_1$–$C_4$ haloalkylsulfonyl, $C_2$–$C_4$ alkoxycarbonyl, $C_2$–$C_4$ alkylaminocarbonyl, $C_3$–$C_5$ dialkylaminocarbonyl, $C_1$–$C_4$ alkylamino, $C_2$–$C_8$ dialkylamino, $C_3$–$C_6$ cycloalkylamino and $C_3$–$C_6$ trialkylsilyl; or each $R^1$ is independently selected from the group consisting of phenyl, benzyl and phenoxy, each optionally substituted with $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $C_2$–$C_4$ haloalkenyl, $C_2$–$C_4$ haloalkynyl, $C_3$–$C_6$ halocycloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ alkylamino, $C_2$–$C_8$ dialkylamino, $C_3$–$C_6$ cycloalkylamino, $C_4$–$C_7$ (alkyl)cycloalkylamino, $C_2$–$C_4$ alkylcarbonyl, $C_2$–$C_6$ alkoxycarbonyl, $C_2$–$C_6$ alkylaminocarbonyl, $C_3$–$C_5$ dialkylaminocarbonyl or $C_3$–$C_6$ trialkylsilyl;

$R^2$ is H; or $C_1$–$C_6$ alkyl, $C_2$–$C_6$ alkenyl, $C_2$–$C_6$ alkynyl or $C_3$–$C_6$ cycloalkyl, each optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino; or $R^2$ is $C_2$–$C_6$ alkylcarbonyl, $C_2$–$C_6$ alkoxycarbonyl, $C_2$–$C_6$ alkylaminocarbonyl or $C_3$–$C_8$ dialkylaminocarbonyl;

$R^3$ is H, $C_1$–$C_6$ alkyl, $C_2$–$C_6$ alkenyl, $C_2$–$C_6$ alkynyl, $C_3$–$C_6$ cycloalkyl, $C_1$–$C_4$ alkoxy, $C_1$–$C_4$ alkylamino, $C_2$–$C_8$ dialkylamino, $C_3$–$C_6$ cycloalkylamino, $C_2$–$C_6$ alkoxycarbonyl or $C_2$–$C_6$ alkylcarbonyl;

$R^4$, $R^5$, $R^6$, $R^7$, $R^8$ and $R^9$ are each independently H, $C_1$–$C_4$ alkyl or $C_1$–$C_4$ haloalkyl;

$R^{10}$ and $R^{11}$ are each independently $C_1$–$C_4$ alkyl or $C_1$–$C_4$ alkoxy;

$R^{12}$ is $C_1$–$C_4$ alkyl, $C_1$–$C_4$ alkoxy or phenyl optionally substituted with one to three substituents selected from the group $R^{17}$;

each $R^{13}$ is independently selected from the group consisting of H, $C_1$–$C_6$ alkyl, $C_3$–$C_6$ cycloalkyl, $C_1$–$C_6$ haloalkyl, halogen, CN, $C_2$–$C_4$ alkoxy, $C_2$–$C_4$ alkoxycarbonyl, $C_1$–$C_4$ alkylthio, $C_1$–$C_4$ haloalkoxy, $C_1$–$C_4$ haloalkylthio, $C_1$–$C_4$ haloalkylsulfinyl and $C_1$–$C_4$ haloalkylsulfonyl;

$R^{14}$ is $C_1$–$C_6$ alkyl optionally substituted with one or more substituents selected from the group consisting of halogen, CN, $NO_2$, hydroxy, $C_1$–$C_4$ alkoxy, $C_1$–$C_4$ alkylthio, $C_1$–$C_4$ alkylsulfinyl, $C_1$–$C_4$ alkylsulfonyl, $C_2$–$C_4$ alkoxycarbonyl, $C_1$–$C_4$ alkylamino, $C_2$–$C_8$ dialkylamino and $C_3$–$C_6$ cycloalkylamino; or phenyl optionally substituted with one to three substituents selected from $R^{17}$; or $R^{14}$ is

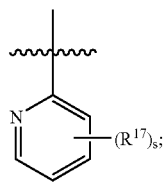

$R^{15}$ is $C_1$–$C_6$ alkyl, $C_3$–$C_6$ cycloalkyl, $C_1$–$C_6$ haloalkyl, halogen, CN, $C_1$–$C_4$ alkoxy, $C_1$–$C_4$ alkylthio, $C_1$–$C_4$ haloalkoxy, $C_1$–$C_4$ haloalkylthio, $C_1$–$C_4$ haloalkylsulfinyl or $C_1$–$C_4$ haloalkylsulfonyl; or $R^{15}$ is phenyl or pyridyl optionally substituted with one to three $R^{17}$;

$R^{16}$ is H, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl or $C_3$–$C_6$ haloalkynyl;

each $R^{17}$ is independently $C_1$–$C_6$ alkyl, $C_3$–$C_6$ cycloalkyl, $C_1$–$C_6$ haloalkyl, halogen, CN, $C_1$–$C_4$ alkoxy, $C_1$–$C_4$ alkylthio, $C_1$–$C_4$ haloalkoxy, $C_1$–$C_4$ haloalkylthio, $C_1$–$C_4$ haloalkylsulfinyl or $C_1$–$C_4$ haloalkylsulfonyl;

m is 0, 1 or 2;

n is 0, 1, 2, 3 or 4;

r is 0 or 1; and s is 0, 1 or 2.

2. The compound of claim 1 wherein A is $S(O)_m$;

one of the $R^1$ groups is attached to the phenyl ring at the 2-position, and said $R^1$ is $C_1$–$C_4$ alkyl, $C_1$–$C_4$ haloalkyl, halogen, CN, $NO_2$, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, $C_1$–$C_4$ haloalkylthio, $C_1$–$C_4$ haloalkylsulfinyl or $C_1$–$C_4$ haloalkylsulfonyl;

$R^2$ and $R^3$ are each independently H, $C_1$–$C_4$ alkyl, $C_2$–$C_4$ alkenyl, $C_2$–$C_4$ alkynyl, $C_3$–$C_6$ cycloalkyl, $C_2$–$C_6$ alkylcarbonyl or $C_2$–$C_6$ alkoxycarbonyl;

$R^4$, $R^5$, $R^6$ and $R^7$ are each independently H or Me;

$R^8$ and $R^9$ are H;

$R^{10}$, $R^{11}$ and $R^{12}$ are Me;

n is 1 or 2; and r is 1.

3. The compound of claim 2 wherein:

each $R^1$ is independently $CH_3$, $CF_3$, $OCF_3$, $OCHF_2$, $S(O)_pCF_3$, $S(O)_pCHF_2$, CN or halogen;

$R^2$ and $R^3$ are H; and is 0, 1 or 2.

4. The compound of claim 3 wherein each $R^{13}$ is H, $CH_3$, $CF_3$, $CH_2CF_3$, $CHF_2$, $OCH_2CF_3$, $OCHF_2$ or halogen;

$R^{14}$ is phenyl optionally substituted with one to two substituents selected from $R^{17}$; or $R^{14}$ is

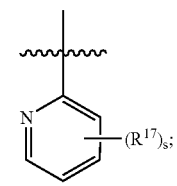

$R^{15}$ and $R^{17}$ are each independently $C_1$–$C_4$ alkyl, $C_1$–$C_4$ haloalkyl, halogen or CN;

each $R^{16}$ is $CH_2CF_3$ or $CHF_2$; and s is 0 or 1.

5. The compound of claim 4 wherein:

each $R^{13}$ is independently halogen, $OCH_2CF_3$, $OCHF_2$ or $CF_3$;

$R^{14}$ is

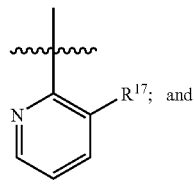

$R^{17}$ is F, Cl or Br.

6. The compound of claim 5 wherein: $R^6$ and $R^7$ are H.

7. The compound of claim 6 wherein: J is J-1, J-2, J-4, or J-8.

8. The compound of claim 7 wherein:
J is J-1;
the $R^1$ attached to the phenyl ring at the 2-position is $CH_3$, F, Cl or Br; a second $R^1$ group is attached to the phenyl ring at the 4-position position, and said second $R^1$ is CN, $CF_3$, F, Cl, Br or I;
$R^{13}$ is independently Cl, Br, $OCH_2CF_3$, or $CF_3$; and
n is 2.

9. A method for controlling an invertebrate pest comprising contacting the invertebrate pest or its environment with a biologically effective amount of a compound of claim 1.

10. The method of claim 9 wherein the invertebrate pest is cockroach, an ant or a termite which contacts the compound by consuming a bait composition comprising the compound.

11. The method of claim 9 wherein the invertebrate pest is a mosquito, a black fly, a stable, fly, a deer fly, a horse fly, a wasp, a yellow jacket, a hornet, a tick, a spider, an ant, or a gnat which is contacted by a spray composition comprising the compound dispensed from a spray container.

12. A composition for controlling an invertebrate pest comprising a biologically effective amount of a compound of claim 1 and at least one additional component selected from the group consisting of a surfactant, a solid diluent, and a liquid diluent, said composition optionally further comprising an effective amount of at least one additional biologically active compound or agent.

13. A spray composition, comprising:
(a) a compound of claim 1; and
(b) a propellant.

14. A bait composition, comprising:
(a) a compound of claim 1;
(b) one or more food materials;
(c) optionally an attractant and
(d) optionally a humectant.

15. A device for controlling an invertebrate pest, comprising:
(a) the bait composition of claim 14; and
(b) a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

16. A composition comprising a compound of claim 1 and at least one additional component selected from the group consisting of a surfactant a solid diluent, and a liquid diluent.

* * * * *